US008415509B2

(12) United States Patent  
Krafft et al.

(10) Patent No.: US 8,415,509 B2
(45) Date of Patent: Apr. 9, 2013

(54) PROCESS FOR PRODUCING DICHLOROPROPANOL FROM GLYCEROL, THE GLYCEROL COMING EVENTUALLY FROM THE CONVERSION OF ANIMAL FATS IN THE MANUFACTURE OF BIODIESEL (75) Inventors: Philippe Krafft, Rhode Saint Genèse (BE); Patrick Gilbeau, Braine-le-Comte (BE); Benoît Gosselin, Tavaux (FR); Sara Claessens, Nieuwerkerken (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 10/580,003

(22) PCT Filed: Nov. 18, 2004

(86) PCT No.: PCT/EP2004/053008
§ 371 (c)(1),
(2), (4) Date: Dec. 19, 2006

(87) PCT Pub. No.: WO2005/054167
PCT Pub. Date: Jun. 16, 2005

(65) Prior Publication Data
US 2007/0112224 A1   May 17, 2007

Related U.S. Application Data (60) Provisional application No. 60/560,676, filed on Apr. 8, 2004.

(30) Foreign Application Priority Data

Nov. 20, 2003  (FR) ...................... 03 13625
Apr. 5, 2004   (FR) ...................... 04 03555

(51) Int. Cl.
*C07C 31/34* (2006.01)
(52) U.S. Cl.
USPC ........................................................ 568/844
(58) Field of Classification Search .................. None
See application file for complete search history.

(56) References Cited

U.S. PATENT DOCUMENTS

| 280,893 | A | 7/1883 | Baujard |
| 865,727 | A | 9/1907 | Queneau |
| 2,060,715 | A | 11/1936 | Arvin |
| 2,063,891 | A | 12/1936 | Dreyfus |
| 2,144,612 | A | 1/1939 | Britton et al. ............ 568/844 |
| 2,198,600 | A | 4/1940 | Britton et al. |
| 2,248,635 | A | 7/1941 | Marple et al. |
| 2,319,876 | A | 5/1943 | Moss |
| 2,444,333 | A | 6/1948 | Castan |
| 2,505,735 | A | 4/1950 | Halbedel |
| 2,726,072 | A | 12/1955 | Hermann |
| 2,811,227 | A | 10/1957 | O'Connor |
| 2,829,124 | A | 4/1958 | Napravnik et al. |
| 2,860,146 | A | 11/1958 | Furman et al. |
| 2,876,217 | A | 3/1959 | Paschall |
| 2,945,004 | A | 7/1960 | Greenlee |
| 2,960,447 | A | 11/1960 | Anderson et al. |
| 3,026,270 | A | 3/1962 | Robinson, Jr. |
| 3,052,612 | A | 9/1962 | Henegar et al. |
| 3,061,615 | A | 10/1962 | Viriot et al. |
| 3,121,727 | A | 2/1964 | Baliker et al. |
| 3,135,705 | A | 6/1964 | Vandenberg |
| 3,158,580 | A | 11/1964 | Vandenberg |
| 3,158,581 | A | 11/1964 | Vandenberg |
| 3,247,227 | A | 4/1966 | White |
| 3,260,059 | A | 7/1966 | Rosenberg, et al. |
| 3,341,491 | A | 9/1967 | Robinson et al. |
| 3,355,511 | A | 11/1967 | Schwarzer |
| 3,385,908 | A | 5/1968 | Schwarzer |
| 3,445,197 | A | 5/1969 | Resh et al. |
| 3,457,282 | A | 7/1969 | Polak et al. |
| 3,618,295 | A | 11/1971 | Geiger et al. |
| 3,711,388 | A | 1/1973 | Gritzner |
| 3,766,221 | A | 10/1973 | Becker |
| 3,839,169 | A | 10/1974 | Moyer |
| 3,865,886 | A | 2/1975 | Schindler et al. |
| 3,867,166 | A | 2/1975 | Sullivan |
| 3,954,581 | A | 5/1976 | Carlin |
| 3,968,178 | A | 7/1976 | Obrecht et al. |
| 4,003,723 | A | 1/1977 | Schafer et al. |

(Continued)

FOREIGN PATENT DOCUMENTS

BE   422877    8/1937
CA   1119320   8/2003

(Continued)

OTHER PUBLICATIONS

English translation of DE 197308, patented Nov. 1908.*
U.S. Appl. No. 12/745,802, filed Aug. 17, 2010.*
K. Weissermel and H J. Arpe in Industrial Organic Chemistry, Third, Completely Revised Edition, VCH, 1997, pp. 149,275.
Industrial Bioproducts: "Today and Tomorrow," Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & sons, Inc.
Ullmann's Encyclopedia of Industrial Chemistry, Fifth, Completely Revised Edition, 1985, vol. A13, pp. 292-293.
The Merck Index, Eleventh Edition, 1989, pp. 759-760.
Ullmann's Encyclopedia of Industrial Chemistry, Fifth Completely Revised Edition, vol. A1, pp. 427-429, 1985.
Ullmann's Encyclopedia of Industrial Chemistry, Fifth Completely REvised Edition, vol. A6, pp. 240-252, 1986.
Hancock, E.G., Propylene and its Industrial Derivatives, 1973, pp. 298-332.

(Continued)

Primary Examiner — Rosalynd Keys
(74) Attorney, Agent, or Firm — Oblon, Spivak, McClelland, Maier & Neustadt, L.L.P.

(57) ABSTRACT

A process for producing dichloropropanol by subjecting glycerol to a reaction with a chlorinating agent in the presence of a carboxylic acid catalyst to produce dichloropropanol, where the carboxylic acid is selected from mono carboxylic acids containing 5 or 6 carbon atoms, dicarboxylic acids selected from glutaric acid and adipic acid, and poly carboxylic acids selected from tri- and tetra-carboxylic acids.

16 Claims, 3 Drawing Sheets

U.S. PATENT DOCUMENTS

| | | | |
|---|---|---|---|
| 4,011,251 A | 3/1977 | Tjurin et al. | |
| 4,024,301 A | 5/1977 | Witenhafer et al. | |
| 4,127,594 A | 11/1978 | Anderson et al. | |
| 4,173,710 A | 11/1979 | Boulet et al. | |
| 4,197,399 A | 4/1980 | Noel et al. | |
| 4,220,529 A | 9/1980 | Daude-Lagrave | |
| 4,240,885 A | 12/1980 | Suciu et al. | |
| 4,255,470 A | 3/1981 | Cohen et al. | |
| 4,390,680 A | 6/1983 | Nelson | |
| 4,405,465 A | 9/1983 | Moore et al. | |
| 4,415,460 A | 11/1983 | Suciu et al. | |
| 4,464,517 A | 8/1984 | Makino et al. | |
| 4,499,255 A | 2/1985 | Wang et al. | |
| 4,595,469 A | 6/1986 | Foller | |
| 4,609,751 A | 9/1986 | Hajjar | |
| 4,634,784 A | 1/1987 | Nagato et al. | 549/521 |
| 4,655,879 A | 4/1987 | Brockmann et al. | |
| 4,935,220 A | 6/1990 | Schneider et al. | |
| 4,960,953 A | 10/1990 | Jakobson et al. | 568/621 |
| 4,973,763 A | 11/1990 | Jakobson et al. | 568/619 |
| 4,990,695 A | 2/1991 | Buenemann et al. | |
| 5,041,688 A | 8/1991 | Jakobson et al. | 568/620 |
| 5,200,163 A | 4/1993 | Henkelmann et al. | |
| 5,278,260 A | 1/1994 | Schaffner et al. | |
| 5,286,354 A | 2/1994 | Bard et al. | |
| 5,344,945 A | 9/1994 | Grunchard | |
| 5,359,094 A | 10/1994 | Teles et al. | |
| 5,393,428 A | 2/1995 | Dilla et al. | |
| 5,445,741 A | 8/1995 | Dilla et al. | |
| 5,478,472 A | 12/1995 | Dilla et al. | |
| 5,486,627 A | 1/1996 | Quarderer, Jr. et al. | |
| 5,567,359 A | 10/1996 | Cassidy et al. | |
| 5,578,740 A | 11/1996 | Au et al. | |
| 5,710,350 A | 1/1998 | Jeromin et al. | |
| 5,731,476 A | 3/1998 | Shawl et al. | |
| 5,744,655 A | 4/1998 | Thomas et al. | |
| 5,779,915 A | 7/1998 | Becker et al. | |
| 5,908,946 A | 6/1999 | Stern et al. | |
| 5,993,974 A | 11/1999 | Fukushima et al. | |
| 6,103,092 A | 8/2000 | Silva | |
| 6,111,153 A | 8/2000 | Crow et al. | |
| 6,142,458 A | 11/2000 | Howk | |
| 6,177,599 B1 | 1/2001 | Cowfer et al. | |
| 6,270,682 B1 | 8/2001 | Santen et al. | |
| 6,288,248 B1 | 9/2001 | Strebelle et al. | |
| 6,288,287 B2 | 9/2001 | Ueoka et al. | |
| 6,350,888 B1 | 2/2002 | Strebelle et al. | |
| 6,350,922 B1 | 2/2002 | Vosejpka et al. | |
| 6,719,957 B2 | 4/2004 | Brady, Jr. et al. | |
| 6,740,633 B2 | 5/2004 | Norenberg et al. | |
| 7,126,032 B1 | 10/2006 | Aiken | |
| 7,128,890 B2 | 10/2006 | Ollivier | 423/488 |
| 7,584,629 B2 | 9/2009 | Sohn et al. | |
| 2001/0014763 A1 | 8/2001 | Ueoka et al. | |
| 2003/0209490 A1 | 11/2003 | Camp et al. | |
| 2004/0016411 A1 | 1/2004 | Joyce et al. | |
| 2004/0024244 A1 | 2/2004 | Walsdorff et al. | |
| 2004/0047781 A1 | 3/2004 | Becenel, Jr. | |
| 2004/0150123 A1 | 8/2004 | Strofer et al. | |
| 2004/0179987 A1 | 9/2004 | Oku et al. | |
| 2004/0232007 A1 | 11/2004 | Carson et al. | |
| 2005/0115901 A1 | 6/2005 | Heuser et al. | |
| 2005/0261509 A1 | 11/2005 | Delfort et al. | |
| 2006/0052272 A1 | 3/2006 | Meli et al. | |
| 2006/0079433 A1 | 4/2006 | Hecht et al. | |
| 2006/0123842 A1 | 6/2006 | Sohn et al. | |
| 2007/0112224 A1 | 5/2007 | Krafft et al. | |
| 2007/0293707 A1 | 12/2007 | Wolfert et al. | |
| 2008/0053836 A1 | 3/2008 | Bulan et al. | |
| 2008/0146753 A1 | 6/2008 | Woike et al. | |
| 2008/0154050 A1 | 6/2008 | Gilbeau | |
| 2008/0281132 A1 | 11/2008 | Krafft et al. | 568/841 |
| 2009/0022653 A1 | 1/2009 | Strebelle et al. | 423/488 |
| 2009/0173636 A1 | 7/2009 | Ooms et al. | |
| 2009/0198041 A1 | 8/2009 | Krafft et al. | |
| 2010/0029959 A1 | 2/2010 | Fan et al. | |

FOREIGN PATENT DOCUMENTS

| | | |
|---|---|---|
| CN | 1296003 A | 5/2001 |
| CN | 101041421 | 9/2007 |
| DE | 180 668 | 1/1906 |
| DE | 197 308 | 11/1906 |
| DE | 238 341 | 3/1908 |
| DE | 197 309 | 4/1908 |
| DE | 1 041 488 | 10/1958 |
| DE | 1 075 103 | 2/1960 |
| DE | 1 226 554 | 10/1966 |
| DE | 2 241 393 | 2/1974 |
| DE | 25 21 813 | 12/1975 |
| DE | 30 03 819 | 8/1981 |
| DE | 216 471 | 6/1983 |
| DE | 32 43 617 | 5/1984 |
| DE | 37 21 003 | 6/1987 |
| DE | 43 02 306 | 8/1994 |
| DE | 43 35 311 | 4/1995 |
| DE | 102 03 914 | 1/2002 |
| DE | 102 54 709 | 6/2004 |
| DE | 238341 | 3/2008 |
| EP | 0 296 341 | 12/1988 |
| EP | 0 347 618 | 12/1989 |
| EP | 0 421 379 | 4/1991 |
| EP | 0 452 265 | 10/1991 |
| EP | 0 518 765 | 12/1992 |
| EP | 0 522 382 | 1/1993 |
| EP | 0 535 949 | 4/1993 |
| EP | 0 563 720 | 10/1993 |
| EP | 0 568 389 | 11/1993 |
| EP | 0 582 201 | 2/1994 |
| EP | 0 618 170 | 10/1994 |
| EP | 0 916 624 | 5/1999 |
| EP | 0 919 551 | 6/1999 |
| EP | 0 774 450 | 2/2000 |
| EP | 1 059 278 | 12/2000 |
| EP | 1 106 237 | 6/2001 |
| EP | 1 153 887 | 11/2001 |
| EP | 1 163 946 | 12/2001 |
| EP | 1 231 189 | 8/2002 |
| EP | 1 298 154 | 4/2003 |
| EP | 0 561 441 | 9/2003 |
| EP | 1 411 027 | 4/2004 |
| EP | 1 752 435 A1 | 2/2007 |
| EP | 1 752 436 A1 | 2/2007 |
| EP | 1 760 060 A1 | 3/2007 |
| EP | 1 762 556 | 3/2007 |
| EP | 1 770 081 A1 | 4/2007 |
| EP | 1 772 446 A1 | 4/2007 |
| EP | 1 775 278 A1 | 4/2007 |
| EP | 2 085 364 | 8/2009 |
| FR | 1 306 231 | 10/1961 |
| FR | 1 417 388 | 10/1964 |
| FR | 1 476 073 | 4/1966 |
| FR | 1 577 792 | 8/1968 |
| FR | 2 180 138 | 5/1973 |
| FR | 2 217 372 | 2/1974 |
| FR | 2 565 229 | 12/1985 |
| FR | 2 752 242 | 2/1998 |
| FR | 2 862 644 | 5/2005 |
| FR | 2 868 419 | 10/2005 |
| FR | 2 869 612 | 11/2005 |
| FR | 2 869 613 | 11/2005 |
| FR | 2 872 504 | 1/2006 |
| FR | 2 881 732 | 8/2006 |
| FR | 2 885 903 | 11/2006 |
| FR | 2 912 743 | 8/2008 |
| FR | 2 913 683 | 9/2008 |
| FR | 2 917 411 | 12/2008 |
| FR | 2 918 058 | 1/2009 |
| FR | 2 925 045 | 6/2009 |
| FR | 2 929 611 | 10/2009 |
| FR | 2 935 699 | 3/2010 |
| FR | 2 935 968 | 3/2010 |
| GB | 14 767 | 1/1914 |
| GB | 404 938 | 7/1932 |
| GB | 406345 | 8/1932 |
| GB | 467 481 | 9/1935 |
| GB | 541357 | 11/1941 |

| | | |
|---|---:|---|
| GB | 679 536 | 9/1952 |
| GB | 736641 | 7/1953 |
| GB | 799 567 | 8/1958 |
| GB | 1046521 | 1/1964 |
| GB | 1083594 | 11/1964 |
| GB | 984446 | 2/1965 |
| GB | 984 633 | 3/1965 |
| GB | 1 387 668 | 3/1972 |
| GB | 1286893 | 8/1972 |
| GB | 1 493 538 | 4/1975 |
| GB | 1 414 976 | 11/1975 |
| GB | 2 173 496 | 10/1986 |
| GB | 702143 | 10/1990 |
| GB | 2 336 584 | 10/1999 |
| GB | 2 885 903 | 11/2006 |
| HU | 2002-003023 | 3/2004 |
| JP | 50-062909 | 5/1975 |
| JP | 55-041858 | 3/1980 |
| JP | 56-29572 | 3/1981 |
| JP | 56-99432 | 8/1981 |
| JP | 61-112066 | 5/1986 |
| JP | 61-236749 | 10/1986 |
| JP | 62-242638 | 10/1987 |
| JP | 63-195288 | 8/1988 |
| JP | 2-137704 | 5/1990 |
| JP | 03-014527 | 1/1991 |
| JP | 03-223267 | 10/1991 |
| JP | 3-223267 | 10/1991 |
| JP | 04-089440 | 3/1992 |
| JP | 04-217637 | 8/1992 |
| JP | 6-25196 | 4/1994 |
| JP | 6-184024 | 7/1994 |
| JP | 06-321852 | 11/1994 |
| JP | 8-59593 | 3/1996 |
| JP | 09-299953 | 11/1997 |
| JP | 10-139700 | 5/1998 |
| JP | 10-218810 | 8/1998 |
| JP | 2000-344692 | 12/2000 |
| JP | 2001-037469 | 2/2001 |
| JP | 2001-213827 | 8/2001 |
| JP | 2001-261308 | 9/2001 |
| JP | 2001-1261581 | 9/2001 |
| JP | 2002-02033 | 1/2002 |
| JP | 2002-038195 | 2/2002 |
| JP | 2002-265986 | 9/2002 |
| JP | 2002-363153 | 12/2002 |
| JP | 2003-81891 | 3/2003 |
| JP | 2003-89680 | 3/2003 |
| JP | 2005-007841 | 1/2005 |
| JP | 2005-097177 | 4/2005 |
| JP | 76021635 | 4/2005 |
| JP | 2007-008898 | 1/2007 |
| JP | 2009-263338 | 11/2009 |
| KR | 900006513 | 11/1987 |
| KR | 2003-29740 | 5/2003 |
| SU | 123153 | 1/1959 |
| SU | 1125226 | 11/1984 |
| SU | 1159716 | 6/1985 |
| SU | 1685969 | 10/1991 |
| WO | WO 95/14639 | 6/1995 |
| WO | WO 96/07617 | 3/1996 |
| WO | WO 96/15980 | 5/1996 |
| WO | WO 97/48667 | 12/1997 |
| WO | WO 98/37024 | 8/1998 |
| WO | WO 99/14208 | 3/1999 |
| WO | WO 99/32397 | 7/1999 |
| WO | WO 00/24674 | 5/2000 |
| WO | WO 01/41919 | 6/2001 |
| WO | WO 01/86220 | 11/2001 |
| WO | WO 02/26672 | 4/2002 |
| WO | WO 03/064357 | 8/2003 |
| WO | WO 2004/056758 | 7/2004 |
| WO | WO 2005/021476 A1 | 3/2005 |
| WO | WO 2005/054167 | 6/2005 |
| WO | WO 2005/097722 | 10/2005 |
| WO | WO 2005/115954 | 12/2005 |
| WO | WO 2005/116004 | 12/2005 |
| WO | WO 2006/020234 | 2/2006 |
| WO | WO 2006/100311 | 9/2006 |
| WO | WO 2006/100311 A2 | 9/2006 |
| WO | WO 2006/100312 A2 | 9/2006 |
| WO | WO 2006/100313 A2 | 9/2006 |
| WO | WO 2006/100314 A1 | 9/2006 |
| WO | WO 2006/100315 A1 | 9/2006 |
| WO | WO 2006/100316 A1 | 9/2006 |
| WO | WO 2006/100317 A1 | 9/2006 |
| WO | WO 2006/100318 A2 | 9/2006 |
| WO | WO 2006/100319 A1 | 9/2006 |
| WO | WO 2006/100320 A2 | 9/2006 |
| WO | WO 2006/106153 A2 | 10/2006 |
| WO | WO 2006/106154 A1 | 10/2006 |
| WO | WO 2006/106155 A2 | 10/2006 |
| WO | WO 2007/054505 | 5/2007 |
| WO | WO 2007/054505 A2 | 5/2007 |
| WO | WO 2007/144335 | 12/2007 |
| WO | WO 2008/101866 | 8/2008 |
| WO | WO 2008/107468 | 9/2008 |
| WO | WO 2008/110588 | 9/2008 |
| WO | WO 2008/145729 | 12/2008 |
| WO | WO 2008/147473 | 12/2008 |
| WO | WO 2008/152043 | 12/2008 |
| WO | WO 2008/152044 | 12/2008 |
| WO | WO 2008/152045 | 12/2008 |
| WO | WO 2009/000773 | 12/2008 |
| WO | WO 2009/016149 | 2/2009 |
| WO | WO 2009/026212 | 2/2009 |
| WO | WO 2009/043796 | 4/2009 |
| WO | WO 2009/077528 | 6/2009 |
| WO | WO 2009/095429 | 8/2009 |
| WO | WO 2009/121853 | 10/2009 |
| WO | WO 2010/029039 | 3/2010 |
| WO | WO 2010/029153 | 3/2010 |
| WO | WO 2010/066660 | 6/2010 |

OTHER PUBLICATIONS

K. Weissermel and H. J. Arpe in Industrial Organic Chemistry, Third, Completely Revised Edition, VCH 1997, pp. 149-163.
K. Weissermel and H. J. Arpe in Industrial Organic Chemistry, Third, Completely Revised Edition, VCH 1997, pp. 275-276.
Ullmann's Encyclopedia of Industrial Chemistry, Fifth Completely Revised Edition, vol. A9, pp. 539-540.
Perry's Chemical Engineers Handbook, Sixth Edition, Robert H. Perry, Don Green, 1984, Section 21-64, to 21-68.
Expert Opinion on the Environment Impact Assessment Documentation Pursuant to Annex No. 5 of Act No. 100/2001 Coll,. as amended by later regulations of the project/intent combined process for the manufacture of epichlorohydrin (SPOLEK) Apr. 2005.
Jeffrey Lutje Spelberg, et al., A Tandem Enzyme Reaction to Produce Optically Active Halohydrins, Epoxides and Diols, Tetrahedron: Asymmetry, Elsevier Science Publishers, vol. 10, No. 15, pp. 2863-2870, 1999.
Oleoline, com, Glycerine Market report, Sep. 10, 2003, No. 62.
Notification Under Act. No. 100/2001, Coll. As Amended by Act No,. 93/2004, Coll. To the extent of Annex No. 4, (SPOLEK) Nov. 30, 2004.
Documentation Under Act No. 100/2001 Coll. As amended by Act No. 93/2004 Coll in the scope of appendix No. 4 (SPOLEK) Jan. 11, 2005.
U.S. Appl. No. 11/914,879, filed Nov. 19, 2007, Gilbeau.
U.S. Appl. No. 11/915,059, filed Nov. 20, 2007, Gilbeau, et al.
U.S. Appl. No. 11/914,836, filed Nov. 19, 2007, Krafft, et al.
U.S. Appl. No. 11/915,067, filed Nov. 20, 2007, Krafft, et al.
U.S. Appl. No. 11/914,874, filed Nov. 19, 2007, Krafft, et al.
U.S. Appl. No. 11/914,862, filed Nov. 19, 2007, Gilbeau.
U.S. Appl. No. 11/914,856, filed Nov. 19, 2007, Krafft, et al.
U.S. Appl. No. 11/914,868, filed Nov. 19, 2007, Krafft.
U.S. Appl. No. 11/915,046, filed Nov. 20, 2007, Krafft, et al.
U.S. Appl. No. 11/914,891, filed Nov. 19, 2007, Krafft, et al.
U.S. Appl. No. 11/915,056, filed Nov. 20, 2007, Gilbeau.
U.S. Appl. No. 11/915,053, filed Nov. 20, 2007, Gilbeau.
U.S. Appl. No. 11/915,088, filed Nov. 20, 2007, Krafft, et al.
U.S. Appl. No. 61/013,680, filed Dec. 14, 2007, Krafft, et al.
U.S. Appl. No. 61/013,704, filed Dec. 14, 2007, Gilbeau, et al.
U.S. Appl. No. 61/013,676, filed Dec. 14, 2007, Borremans.
U.S. Appl. No. 61/013,707, filed Dec. 14, 2007, Krafft, et al.

U.S. Appl. No. 61/013,672, filed Dec. 14, 2007, Krafft, et al.
U.S. Appl. No. 61/013,713, filed Dec. 14, 2007, Gilbeau.
U.S. Appl. No. 61/013,710, filed Dec. 14, 2007, Krafft, et al.
U.S. Appl. No. 12/529,777, filed Sep. 3, 2009, Krafft, et al.
U.S. Appl. No. 12/529,778, filed Sep. 3, 2009, Krafft, et al.
Gibson., "The Preparation, Properties, and Uses of Glycerol Derivatives. Part III. The Chlorohydrins", Chemistry and Industry, Chemical Society, pp. 949-975, 1931.
Carre et al., "La Transformation Des Alcools Polyatomiques En Mono-Et En Polychlorhydrines Au Moyen Du Chlorure De Thionyle", Bull. Soc. Chim. Fr., No. 49, pp. 1150-1154, 1931.
Fauconnier, "Preparation De L'Epichlorhydrine", Bull. Soc. Chim. Fr., No. 50, pp. 212-214, 1888.
Bonner et al., "The Composition of Constant Boiling Hydrochloric Acid At Pressures of 50 to 1220 Millimeters", Journal of American Chemical Society, vol. 52, pp. 633-635, 1930.
E. Milchert et al., "Installation for the Recovery of Dichloropropanols and Epichlorohydrin from the Waste Water in Epichlorohydrin Production", Pol. J. Appl. Chem., vol. 41, p. 113-118 (1997).
Klaus Weissermel, et al., "Industrial Organic Chemistry," ($3^{rd}$ Completely Revised Edition); VCH 1997. p. 93-98.
Klaus Weissermel, et al., "Industrial Organic Chemistry," ($3^{rd}$ Completely Revised Edition); VCH 1997. p. 276-277.
Klaus Weissermel, et al., "Industrial Organic Chemistry," ($3^{rd}$ Completely Revised Edition); VCH 1997. p. 347-355.
U.S. Appl. No. 12/502,296, filed Jul. 14, 2009, Krafft, et al.
U.S. Appl. No. 12/502,342, filed Jul. 14, 2009, Krafft, et al.
U.S. Appl. No. 12/527,538, filed Aug. 17, 2009, Gilbeau, et al.
Kirk-Othmer Encyclopedia of Chemical Technology, Third Edition, vol. 4, Blood, Coagulants and Anticoagulants to Cardiovascular Agents, 1978, pp. 847-848.
Medium and Long-Term Opportunities and Risks of the Biotechnologial Production of Bulk Chemicals from Renewable Resources—The Potential of White Biotechnology—The BREW Project—Final Report—Prepared under the European Commission's GRXTH Programme (DG Research) Utrecht, Sep. 2006 (pp. 29-31).
Ullmann Encyl. Industr. Chem., $5^{th}$ Ed., vol. A6, (1988), pp. 401-477.
Polymer Science Dictionary, M.S.M., Elsevier Applied Chemistry, London and New York 1989, p. 86.
Perry's chemical Engineers' Handbook, Sixth Edition, Section 21, pp. 21-55, 1984.
Ying Ling Liu, "Epoxy Resins from Novel Monomers with a Bis-(9,10-dihydro-9-oxa-10-oxide-10-phosphaphenanthrene-10-yl-) Substituent," Journal of Polymer Science: Part A: Polymer Chemistry, vol. 40, 359-368 (2002).
Ying Ling Liu, "Phosphorous-Containing Epoxy Resins from a Novel Synthesis Route," Journal of Applied Polymer Science, vol. 83, 1697-1701 (2002).
U.S. Appl. No. 12/663,753, filed Dec. 9, 2009, Krafft, et al.
U.S. Appl. No. 12/663,744, filed Dec. 9, 2009, Boulos, et al.
U.S. Appl. No. 12/663,749, filed Dec. 9, 2009, Krafft, et al.
U.S. Appl. No. 12/663,887, filed Dec. 10, 2009, Krafft, et al.
Derwent Publications, AN 109:6092 CA, JP 62-242638, Oct. 23, 1987.
Derwent Publications, AN 1987-338139 [48], JP 62-242638, Oct. 23, 1987.
J.B. Conant et al., "Glycerol a,y-Dichlorophydrin," Organic Syntheses Coll., vol. 1, p. 292, 1941.
I. Miyakawa et al., Nagoya Sangyo Kagaku Kenkyusho Kenkyu Hokoku, 10, 49-52 (1957).
Han Xiu-Ying et al., Shanxi Daxue Xueba Bianjibu, 2002, 25(4), 379-80).
Semendyava, n. D. et al., Khimicheskaya Promyshlennost, Seriya: Khornaya Promyshlennost (1981), 5, 21-2 (CA Summary) XP 002465275.
Rudnenko, E.V., et al., Kakokrasochnye Materialy I Ikh Primenenie (1988), 4, 69-71 (CA Summary) XP 002465276.
Armando Novelli, "The preparation of mono- and dichlorohydrins of glycerol", Anal . farm. bioquim., vol. 1, 1930, pp. 8-19 (with English Abstract).
Herman A. Bruson, et al., "Thermal Decomposition of Glyceryl Carbonates," Journal of the American Chemical Society, vol. 74, Apr. 1952 pp. 2100-2101.
Kirk Othmer Encyclopedia of Chemical Technology, Third Edition, vol. 12, 1980, pp. 1002-1005.
Chemical Engineering Handbook, the $6^{th}$ Edition, Edited by the Chemical Engineers, published by Maruzen Co., Ltd., 1999, pp. 1296-1306 w/English translation of p. 1296, Table 28.4, p. 1298, left column, lines 4-13 and p. 1305, Table 28.10.
Product Brouchure of De Dietrich Company, Apr. 1996, pp. 3, 8 and 9 w/English translation of p. 8, left column, lines 1-4, p. 9.
The Journal of the American Chemical Society, vol. XLV, Jul.-Dec. 1923, pp. 2771-2772.
M. Schellentrager, "Untersuchungen zur oxidation Entfarbung aus gewahlter Reaktivfarbstoffe: Analyse der Abbauprodukte miteels hochauflosender LC-MS", Diisertation, XP002548413 (Jan. 1, 2006) w/Attached English Abstract.
Perry's Chemical Engineers Handbook $7^{th}$ Ed. $11^{th}$ Section, 1997.
Perry's Chemical Engineers Handbook $7^{th}$ Ed. $13^{th}$ Section, 1997.
Perry's Chemical Engineers Handbook $7^{th}$ Ed. $15^{th}$ Section, 1997.
Ullmann Encyclopedia Industr. Chem. $5^{th}$ Ed., vol. A23, 1993 pp. 634, 635 & 637.
Ullmann Encyclopedia Industr. Chem. $5^{th}$ Ed., vol. A13, 1989 pp. 289.
Ullmann Encyclopedia Industr. Chem. $5^{th}$ Ed., vol. All, 1988 pp. 354-360.
U.S. Appl. No. 12/304,391, filed Dec. 11, 2008, Krafft, et al.
Myszkowski J. et al., "Removal of Chlorinated Organic Impurities from Hydrogen Chloride," CA, Mar. 1986, XP002352444 (English CA Summary only).
Myszkowski J. et al., "Removal of Organic Compoiunds from Gaseous Hydrogen Chloride by an Absorption Method," CA, XP002352445 (English CA summary only), 1986.
Milchert E. et al., "Recovering Hydrogen Chloride and Organic Chlor Compounds from the Reaction Mixture in the Chlorination of Ethylene," CA, XP002352443 (English CA summary only). Jan. 1994.
Laine D.F., et al., "The Destruction of Organic Pollutants Under Mild Reaction Conditions ; A Review, " Microchemical Journal, vol. 85, No. 2, 2006, pp. 183-193.
Epoxy Resins, Shanghai Resin Plant, Shangai People's Press, 1971.
Martinetti Richard et al., "Environment Le Recyclage De l'eau," Industrie Textile, Ste. Sippe Sarl, Metz, FR., No. 1300, Jul. 1, 1998, ISSN: 0019-9176.
12093 Chemicals, Chemical Daily Co., Ltd. (Published on Jan. 22, 1993) with attached English translation of relevant excerpts.
Chemicals Guide, Chemical Daily Co., Ltd. (Published on Jun. 15, 1990) with attached English translation of relevant excerpts.
Robert T. Morrison & Robert N. Boyd, Organic Chemistry, vol. II, pp. 666 to 667 and 712 to 714 (Japanes translation), published on Jul. 10, 1970, Tokyo Kagaku Dozin Co., Ltd. (Similar passages but retrieved from the English $5^{th}$ Edition of the Book, 1987. pp. 701, 702, 841, 842, 844, & 845.
U.S. Appl. No. 12/600,018, filed Nov. 13, 2009, Borremans, et al.
U.S. Appl. No. 12/681,083, filed Mar. 31, 2010, Bobet, et al.
U.S. Appl. No. 12/745,802, filed Jun. 2, 2010, Gilbeau, et al.
Ullmann's Encyclopedia of Industrial Chemistry, 2005, Wiley-VCH GmbH & Co., KgaA, Weinhem, pp. 8-15 and 401-477, Published online Mar. 15, 2001.
RD 436093, Aug. 10, 2000, Research Disclosure.
U.S. Appl. No. 12/864,211, filed Jul. 27, 20120, Gilbeau, et al.
Ma Zengxin, Gan Yicui, Recovery of Polyglycerol from Residues of Synthetic Glycerol—Riyong Huaxue Gongye, 1997, 4, 21023 (Abstract Only).
U.S. Appl. No. 12/935,538, Sep. 29, 2010, Gilbeau, et al.
W. Giger et al., "14C/12C-Ratios in Organic Matter and Hydrocarbons Extracted from Dated Lake Sediments," Nuclear Instruments and Methods in Physics Research B5 (1984), 394-397. XP-002631954.
Jurgen O. Metzger, "Fats and Oils as Renewable Feedstock for Chemistry," Eur. J. Lipid Sci. Technol. (2009), 111, 865-876. XP-002631953.

Bruce M. Bell, "Glycerin as a Renewable Feedstock for Epichlorohydrin Production. The GTE Process," Clean-Soil, Air, Water, vol. 36, No. 8, (2008) pp. 657-661. XP-002631952.

Sang Hee Lee, et al., "Direct Preparation of Dichloropropanol (DCP) from Glycerol Using Heteropolyacid (HPA) Catalysts: A Catalyst Screen Study," Catalysis Communications (9), 2008, 1920-1923.

U.S. Appl. No. 13/131,516, May 26, 2011, Gilbeau, et al.

Vinnolit; Vinnolit receives EU grant for water recycling project; Press Release, 2008: http://www.vinnolit.de/vinnolit.nsf/id/EN_Vinnolit_receives_EU_grant_for_water_recycling_project_.

N. W. Ziels, Journal of American Oil Chemists' Society, Nov. 1956, vol. 33, pp. 556-565.

U.S. Appl. No. 13/060,421, Feb. 23, 2011, Balthasart, et al.

Perry's Chemical Engineers Handbook, Sixth Edition, McGraw Hill Inc., (1984) Section 18.

vol. B3: Unit Operations II of Ullmann's Encyclopedia of Industrial Chemistry, Fifth Completely Revised Edition, Published by VCH, 1988, pp. 8-20 and 8-21.

U.S. Appl. No. 13/051,007, Mar. 18, 2011, Krafft, et al.

U.S. Appl. No. 13/063,230, Mar. 10, 2011, Krafft, et al.

New Experimental Chemical Course 1, Basic Operation I, Section 4, Separation and Purification, pp. 251-252, Issued Sep. 20, 1975 (with English Translation).

Copyright Mar. 1992, Advanced Organic Chemistry, 4$^{th}$ Ed., pp. 889, 908 and 937.

Yong, K.C., et al., "Refining of Crude Glycerine Recovered from Glycerol Residue by Simple Vacuum Distillation," Journal of Oil Palm Research, vol. 13, No. 2, Dec. 2001, pp. 39-44.

F. Krausz Ann. De Chimie, 12e série, t. Nov.-Dec. 4, 1949, pp. 811-931.

Glycerin: An overview, Soap and Detergent Association. Copyright 1990 by the Soap and Detergent Association. pp. 1-26.

Chemical and Engineering News, 1948, 26 (38), pp. 2770-2771.

Fairbourn et al., "The Partial Esterification of Polyhydric Alcohols. Part XII. The Function of Ethylene-oxide Rings," J. Chem. Soc. 1932, pp. 1965-1972, Received, Apr. 6, 1932.

Clarke et al., Organic Syntheses, Coll., vol. 1, p. 233, (1941); vol. 3, p. 47, (1923).

Braun, Organic Syntheses, Coll., vol. 2, p. 256, (1943); vol. 6, p. 30, (1936).

Conant et al. Organic Syntheses, Coll vol. 1, p. 292, (1941); vol. 2, p. 29, (1922).

Bull. Soc. Chim. Fr. (1943), 10, pp. 52-58, with English Translation.

"Chemical Properties and Derivatives of Glycerol", (1965), published by Glycerine Producers' Association in New York, pp. 1-20.

G.W. Busby and D.E. Gosvenor, "The Purification of Glycerin by Ion-Exchange," The Journal of The American Oil Chemists' Society, vol. 29, No. 8, pp. 318-320 (1952).

L.L. Lamborn, "Modern Soaps, Candles and Glycerin," D. Van NOstrand Company, London, third edition 1918, pp. 542-550, 573-574.

Knothe, "Historical perspectives on vegetable oil-based diesel fuels", Inform, vol. 12, Nov. 2001. pp. 1103-1107.

U. Schuchardt et al., "Transesterification of Vegetable Oils: a Review," J. Braz. Chem. Soc., vol. 9, No. 1, 199-210, 1998.

S. Claude, "Research of new outlets for glycerol—recent developemnts in France," Fett/Lipid 101 (1999), Nr. 3, S 101-104.

C.B. Prakash,"A critical review of Biodiesel as a Transportation Fuel in Canada," for the Transportation Systems Branch Air Pollution Prevention Directorate Enviornment Canada, Mar. 25, 1998, pp. 1-104.

Fukuda et al., "Biodiesel Fuel Production by transesterification of Oils", Journal of Bioscience and Bioengineering, vol. 92, No. 5, pp. 405-416 (2001).

Azeotropic Data-III Compiled by Lee H. Horsley, The Dow Chemical Co., Midland, Mich., American Chemical Society (1973).

Yoshikazu Suzawa et al., Kagachu Sohchi (Chemical Apparatuses), vol. 23, No. 11, 3744, (published on Nov. 1981) with English translation.

Journal of American Oil Chemists' Society Jul. 1982, vol. 59, No. 7 pp. 292-295.

Chemical Engineering Handbook, 6th Revised Edition, 2nd print issued on Apr. 25, 2001, with attached English translation.

R. A. Kiseleva and V.M. Goncharko, J. Appl. Chem. USSR, 1971, vol. 44, pp. 2086-2090.

Boschan and S. Winstein, Journal of the American Chemical Society, 1956, vol. 78, pp, 4921-4925.

"Electrolytic cell test for electrolysis of epoxy sewage salt to prepare chlor-alkali", process Equipment Department of Research Institute of chlor-alkali, Shengyang chemical Plant, Liaononhg Chemical Industry, Issue No. 2, pp. 32-37, published Dec. 31, 1981, with attached English translation.

"Analysis of the Composition of the Byproduct During the Manufacturing Process of Sepichlorhydrin by GC-MS", Ren Chengxin et al., Chemical Analysis and Measurement, vol. 12, Issue No. 3, p. 25-26, Dec. 31, 2003, with attached English translation.

U.S. Appl. No. 13/238,206, Sep. 21, 2011, Gilbeau, et al.

Dr. Armando Novelli, "On the Preparation of Glycerol Mono- and Dichlorohydrins," Anales de Farmacia y Bioquimica 1 (1930), pp. 6-19 (with English Translation).

The State Intellectual Property Office of The People's Republic of China, Application No. 200480034393.2, Issue No. 2011042200250440. Case No. 4W100871, Date of Notification: Apr. 22, 2011.

The State Intellectual Property Office of the People's Republic of China, Application No. 200480034393.2, Issue No. 2011060200507110, Case No. 4W100871, Date of Notification: Jun. 8, 2011.

Encyclopedia of Chemical Technology, vol. 5, Nov. 1993/Annex 6 YN, Glycerol; Glycerin;Propane-1, 2, 3-triol, 3 pages.

Manufacture and use of epoxy resin, edited by Shanghai Resin Factory, published by China Petrochemical Press, First Edition, Oct. 1974, pp. 1-10.

Handbook of Chemical Products, Heavy Organic Chemicals, Second edition, published by Chemical Industry Press, Jan. 1995, pp. 1-9.

Handbook of Azeotropic Mixture, edited by Information Department of Comprehensive Scientific Technology Research Institution of Fushun City, 1993, 5 pages.

Encyclopedia for Chinese Adult Education, 1994, Organic and High Molecular Chemical Products, 6 pages.

* cited by examiner

PROCESS FOR PRODUCING DICHLOROPROPANOL FROM GLYCEROL, THE GLYCEROL COMING EVENTUALLY FROM THE CONVERSION OF ANIMAL FATS IN THE MANUFACTURE OF BIODIESEL

The present application is a 371 of PCT/EP04/53008 filed Nov. 18, 2004, and claims benefit of U.S. provisional patent application 60/560,676 filed Apr. 8, 2004.

The present invention relates to processes for producing an organic compound, in particular to a process for producing dichloropropanol.

It is known that natural petrochemical resources, for example oil or natural gas, that are available on earth are limited. Now, these resources are used for producing fuels and as a starting product for producing a large variety of useful organic compounds such as monomers or reactants for producing plastics, for example epichlorohydrin or dichloropropanol (see, for example, Ullmann's Encyclopedia of Industrial Chemistry, 5. ed., Vol. A9, p. 539-540). Documents Chemistry and Industry, Nov. 20, 1931, Part III, pages 949 to 954, and Nov. 27, 1931, Part III, pages 970 to 975, describe a process for the synthesis of dichloropropanol from glycerol and hydrochloric acid in the presence of acetic acid as acid catalyst.

According to known processes for producing dichloropropanol, the product is generally obtained in highly diluted solution with a titre of 5 to 15% by weight. It is then particularly expensive to purify it Moreover, the major isomer obtained according to such processes is 2,3-dichloropropane-1-ol.

It was desirable to find uses and processes making it possible to reduce the consumption of natural petrochemical resources, in particular for the abovementioned uses.

It was also desirable to find processes for re-using by-products of other production processes so as to minimize the overall amount of by-products having to be eliminated or destroyed.

Consequently, the invention relates to the use of glycerol obtained from renewable raw materials, as a staring product for producing organic compounds.

The use according to the invention makes it possible to obtain a large number of organic compounds while at the same time minimizing the consumption of natural oil resources. The glycerol derived from renewable raw materials can be readily and effectively used in reactions for producing organic compounds, in particular organic compounds comprising a number of carbon atoms which is a multiple of 3. If necessary, the crude glycerol can be readily purified with a view to it being used in the production of organic compounds.

The expression "glycerol obtained from renewable raw materials" is intended to denote in particular glycerol obtained in the course of the production of biodiesel, or else glycerol obtained during conversions of fats or oils of plant or animal origin in general, such as saponification, trans-esterification or hydrolysis reactions. A particularly suitable glycerol can be obtained during the conversion of animal fats. Another particularly suitable glycerol can be obtained during the production of biodiesel.

In contrast, synthetic glycerol is generally obtained from petrochemical resources.

In the use according to the invention, the glycerol can be a crude product or a purified product. When the glycerol is a crude product, it can comprise, for example, water and a metal salt, in particular a metal chloride, which is preferably chosen from NaCl and KCl. The metal salt can also be selected from metal sulphates such as sodium sulphate and potassium sulphate. The crude product can also contain organic impurities such as carbonyl compounds, in particular aldehydes, fatty acids, or esters of fatty acids, such as in particular monoglycerides or diglycerides, optionally in combination with water and/or the metal chloride.

In the use according to the invention, the crude product generally comprises at least 40% by weight of glycerol. Often, the crude product comprises at least 50% by weight of glycerol. Preferably, it comprises at least 70% by weight of glycerol. Often, the crude product comprises at most 99% by weight of glycerol. Typically, it comprises at most 95% by weight of glycerol.

In the use according to the invention, the crude product generally comprises at least 5% by weight of water or, in the absence of other compounds, at least 1% by weight of water. In the use according to the invention, the crude product generally comprises at most 50% by weight of water or, in the absence of other compounds, at most 60% by weight of water. Often, the crude product comprises at most 30% by weight of water, preferably at most 21% by weight of water.

In another embodiment, the crude product comprises at most 89% by weight of glycerol. In that embodiment, the crude product comprises at most 85% by weight of glycerol. In that embodiment, the crude product comprises generally at least 10% by weight of water and often at least 14% by weight of water.

Where appropriate, the crude product generally has a metal salt, in particular a metal chloride content of at least 1% by weight, preferably greater than or equal to approximately 3% by weight. Where appropriate, the crude product generally has a metal salt, in particular a metal chloride content of at most 10% by weight, preferably less than or equal to approximately 5% by weight.

When purified glycerol is used in the use according to the invention, said glycerol is obtained, staring with the crude product, by means of one or more purification operations such as a distillation, an evaporation, an extraction, or else a concentration operation followed by a separation operation such as settling out, filtration or centrifugation. A distillation operation gives good results. It is also possible to carry out an operation consisting in drying the crude product or the product derived from the purification operations. It is also possible to carry out a purification operation which comprises treating the crude product or a product obtained from another purification operation, with a resin. An example of such a treatment is a chromatography operation over an ion-exchange resin, in particular an anion exchange resin.

In the use according to the invention, the purified product generally comprises at least 80% by weight of glycerol. It preferably comprises at least 90% by weight of glycerol. Often, the purified product comprises at most 99.9% by weight of glycerol. It can comprise at most 97% by weight of glycerol. It can also comprise at most 95% by weight of glycerol.

In the use according to the invention, the purified product generally comprises at least 0.1% by weight of water. In the use according to the invention, the purified product generally comprises at most 20% by weight of water. Often, the purified product comprises at most 10% by weight of water. It preferably comprises at most 5% by weight of water. In a particular variant, the purified product comprises at most 3% by weight of water.

In a preferred variant of the use according to the invention, the purified glycerol product generally comprises at most 0.5% by weight of aldehydes. It preferably comprises at most 0.1% by weight of aldehyde. Often, the purified glycerol product generally comprises at least 1 mg/kg by weight of aldehydes.

It has been found particularly advantageous to reduce the content or totally remove aldehydes possibly present in the crude product, during an evaporation step for instance. This allows to obtain less coloured products from the use according to the invention.

In a variant of the use according to the invention, the glycerol contains at least one other alcohol, preferably chosen from methanol and ethanol. The alcohol content in the purified product may, for example, be at least 10 mg/kg. Generally, this content is less than or equal to 10% by weight. A content of another alcohol of less than or equal to 1000 mg/kg is preferred.

The use according to the invention applies in particular to the production of organic compounds comprising a number of carbon atoms which is a multiple of 3. In a first preferred embodiment, the organic compound comprises 3 carbon atoms. In a second preferred embodiment, the organic compounds comprise 6, 9, 12, 15 or 18 carbon atoms, preferably 6, 9 or 12 carbon atoms.

The use according to the invention also applies in particular to the production of oxygenated organic compounds preferably comprising a number of carbon atoms as described above.

The use according to the invention applies particularly preferably to the production of chlorinated compounds such as dichloropropanol and epichlorohydrin. Surprisingly, the use according to the invention makes it possible to economically obtain these compounds staring from renewable resources.

Consequently, the invention also relates to a process for producing an organic compound, comprising the use according to the invention.

Consequently, the invention also relates in particular to a method for producing a chlorinated organic compound, according to which glycerol obtained from renewable raw materials is used, in accordance with the use according to the invention, and said glycerol is brought into contact with at least one chlorinating agent. It is understood that the methods of production described hereinafter can also be carried out with glycerol in general and are not limited to the preferred use of glycerol obtained from renewable raw materials.

In the process for producing a chlorinated organic compound according to the invention, the chlorinating agent may be an agent for oxidative chlorination or substitutive chlorination. An agent for substitutive chlorination is preferred.

Among the agents for oxidative chlorination, mention may in particular be made of chlorine.

Among the agents for substitutive chlorination, mention may in particular be made of a chlorinating agent comprising hydrogen chloride.

This chlorinating agent is particularly advantageous, since it is often obtained as a by-product in organic chlorination, elimination or substitution reactions, or else by combustion. The present invention makes it possible to valorize this by-product.

In a first variant, the chlorinating agent is substantially anhydrous hydrogen chloride.

This variant is particularly advantageous when the production takes place on the same site as a production of hydrogen chloride, for example a production of vinyl chloride or of 4,4-methylenediphenyl diisocyanate (MDI), which provides hydrogen chloride as a by-product.

In a second variant, the chlorinating agent is an aqueous solution of hydrogen chloride. In this case, the hydrogen chloride content of the solution is generally at least 4% by weight. Preferably, this content is greater than or equal to 20% by weight. In this case, the hydrogen chloride content of the solution is generally at most 37% by weight.

This particular aspect makes it possible to valorize low-quality hydrochloric acid derived, for example, from the pyrolysis of chlorinated organic compounds or having been used for stripping metals.

In particular, it is possible to use hydrochloric acid loaded with dichloropropanol originating, for example, from a reaction for producing dichloropropanol by hypochlorination of the allyl chloride, according to the usual process for synthesizing this product.

In a particular aspect, concentrated hydrochloric acid, generally comprising from 28 to 37% by weight of hydrogen chloride, is used as a primary source of the chlorinating agent, and said concentrated hydrochloric acid is separated, for example by evaporation, into at least two fractions, the first consisting essentially of anhydrous hydrogen chloride and the second comprising hydrogen chloride and water in proportions in which they form an azeotrope, said azeotrope consisting, at a pressure of 101.3 kPa, of 19 to 25% of hydrogen chloride and of 75 to 81% by weight of water, in particular of approximately 20% by weight of hydrogen chloride and of approximately 80% of water.

This particular aspect makes it possible to use a readily transportable chlorinating agent while at the same time allowing an effective control of the water content in the reaction medium, in particular when the reaction between the glycerol and the chlorinating agent is carried out in several steps.

In a third variant, the chlorinating agent is hydrogen chloride generated in situ within the reaction medium, for example starting with an inorganic acid such as sulphuric acid or phosphoric acid, and a suitable metal chloride such as NaCl, KCl or $CaCl_2$.

These various variants may be combined; thus, for example, a supply of aqueous HCl can be completed with a supply of gaseous and/or anhydrous HCl.

The process for producing a chlorinated organic compound according to the invention is generally carried out in a reactor made of or coated with materials that are resistant, under the reaction conditions, to the chlorinating agents, in particular to hydrogen chloride.

By way of suitable material, mention may be made, for example, of enamelled steel. Polymers may also be used. Among the polymers, polyolefins such as polypropylene, and in particular fluorinated polymers such as polytetrafluoroethylene, poly(vinylidene fluoride) and poly(perfluoropropylvinylether), and polymers comprising sulphur, such as polysulphones or polysulphides, that are in particular aromatic, are very suitable.

Coatings by means of resins can be used effectively; among these, epoxy resins or phenolic resins are particularly suitable.

Certain metals or alloys thereof may also be suitable. Mention may in particular be made of tantalum, titanium, copper, gold and silver, nickel and molybdenum, in particular alloys containing nickel and molybdenum. They may be used within the mass, or in the form of cladding, or else by means of any coating process.

Ceramics or metalloceramics and also refractory materials can also be used.

For certain specific components, for example heat exchangers, graphite, which may or may not be impregnated, is particularly suitable.

In the process for producing a chlorinated organic compound according to the invention, the reaction between the glycerol and the chlorinating agent may be carried out in the presence or in the absence of a catalyst. It is preferred to carry out the reaction in the presence of a suitable catalyst.

In this case, a catalyst based on carboxylic acid or on carboxylic acid derivatives, such as a carboxylic acid anhydride, a carboxylic acid chloride, a carboxylic acid salt or a carboxylic acid ester, is advantageously used. The carboxylic acid in the catalyst generally comprises from 1 to 20 carbon atoms. It preferably comprises 1, 2, 3, 4, 5, 6, 7 or 8 carbon atoms. The carboxylic acid preferably contains more than 4 carbon atoms. An acid or acid derivative having an atmospheric boiling point of greater than or equal to 200° C., preferably greater than or equal to 220° C., is very suitable. Generally, the acid or acid derivative is soluble in the reaction medium at the reaction temperature. Preferably, this acid or acid derivative does not form an azeotrope with water.

The Henry's constant of the catalyst, in particular the acid or acid derivative at 25° C. is generally less than or equal to $10^{-6}$ atm.m$^3$.mol$^{-1}$, preferably less than or equal to $10^{-8}$ atm.m$^3$.mol$^{-1}$. This variant makes it possible in particular to draw off the water and the chlorinated organic compound produced, while at the same time conserving virtually all the catalyst in the reaction medium, and particularly good conversions of glycerol to desired product can be obtained. The chlorinated organic compound produced can be readily recovered with a high purity.

Particular examples of catalysts are based on at least one carboxylic acid chosen from acetic acid, formic acid, propionic acid, butyric acid, fatty acids and aromatic carboxylic acids such as benzoic acid, that are optionally substituted.

Another particular example of carboxylic acids are poly (carboxylic acids) such as di-, tri- or tetracarboxylic acids. Dicarboxylic acids are preferred.

In a first embodiment, the catalyst is based on acetic acid

In a second preferred embodiment, the catalyst is based on substituted benzoic acid. In this embodiment, the aromatic ring often carries at least one substituent in the 2- or 4-position. This substituent is advantageously among the inductive and mesomeric capturing groups such as a nitro group, or among the mesomeric donating and inductive capturing groups such as a hydroxyl group, an alkoxy group, such as methoxy group, or the halogens such as chlorine and fluorine, or an optionally alkylated amino group, and among these, in particular a di- or trialkylamino group.

Specific examples of catalysts are chosen from salicylic acid, 4-chlorobenzoic acid, 2,4-dichlorobenzoic acid, 4-nitrobenzoic acid and 2,4-dinitrobenzoic acid.

In a third preferred embodiment, the catalyst is based on a fatty acid. Preferred examples are chosen from butyric acid, valeric acid, caproic acid, heptanoic acid, octanoic (caprylic) acid, lauric acid, decanoic acid or mixtures thereof. Octanoic (caprylic) acid is a particularly preferred example of such an acid.

In a fourth preferred embodiment, the catalyst is based on a poly(carboxylic acid). Preferred examples are chosen from succinic acid, glutaric acid and adipic acid. Adipic acid is preferred.

Pure or purified catalyst can be introduced into the reactor as such or in solution in one of the reactants such as for example glycerol or aqueous hydrochloric acid or in an appropriate solvent for example selected from water, glycerol monochlorohydrin and dichloropropanol. The addition of the catalyst can be performed in a continuous or discontinuous way.

The catalyst concentration in the reaction medium can suitably be optimized in order to minimise the reaction medium volume. The expression "catalyst concentration" is intended to denote the concentration of the acid and of its derivatives (esters for instance). The catalyst concentration is expressed in mol of acid and acid derivative, in particular ester moieties per kg of liquid reaction medium. This concentration is generally higher than or equal to 0.1 mol/kg, preferably higher than or equal to 1 mol/kg and most preferably higher than or equal to 2 mol/kg. The catalyst concentration as defined above is usually lower than or equal to 10 mol/kg, specifically lower than or equal to 8 mol/kg and more specifically lower than or equal to 4 mol/kg.

In particular, the second, third and fourth preferred embodiments make it possible to obtain a good yield of desired product, in particular when the reaction is carried out continuously, and to readily separate this product from the reaction medium and from the catalyst. In particular in the fourth embodiment, it is possible to obtain, at the end of the reaction, a chlorinated organic compound of very high purity, optionally as a mixture with water. It is often possible to introduce said chlorinated organic compound, in particular dichloropropanol, without prior purification, into a subsequent reaction step, for example for producing epichlorohydrin.

In the process according to the invention, the reaction is generally carried out at a temperature of at least 20° C. This temperature is often at least 60° C. It is preferably at least 80° C. A temperature of greater than or equal to approximately 90° C. is more particularly preferred. In the process according to the invention, the reaction is generally carried out a temperature of at most 160° C. This temperature is often at most 140° C. It is preferably at most 120° C.

In another embodiment, the reaction is carried out at a temperature of greater than or equal to 110° C. This temperature is often greater than or equal to 115° C. It is preferably greater than or equal to approximately 120° C. In this embodiment, the reaction is generally carried out at a temperature of at most 160° C. This temperature is often at most 140° C. It is preferably less than or equal to approximately 130° C.

This embodiment is particularly preferred when the reaction is carried out continuously.

In still another embodiment, the reaction is carried out at a temperature of greater than or equal to 160° C. This temperature is often greater than or equal to 170° C. It is preferably greater than or equal to approximately 180° C. In this embodiment, the reaction is generally carried out at a temperature of at most 300° C.

In the process according to the invention, the reaction is generally carried out at a pressure of at least 0.3 bar. The reaction is often carried out at a pressure of at least 0.5 bar. This pressure is preferably greater than or equal to approximately 1 bar (atmosphere pressure). In the process according to the invention, the reaction is generally carried out at a pressure of at most 100 bar. This pressure is often at most 20 bar. It is preferably at most 15 bar and most preferably at most 10 bar.

In particular when hydrogen chloride is used as the chlorination agent, reaction products in the process for producing a chlorinated organic compound are sufficiently stable to allow for combination of high reaction pressure and high reaction temperature thereby allowing to reduce the volume of equipments.

In a preferred first aspect of the process according to the invention, the reaction is carried out under a slight vacuum as described above. This makes it possible in particular to remove the water from the reaction medium as it forms or as the reaction progresses.

In a second preferred aspect of the process according to the invention, the reaction is carried out under an increased pressure as described above. This makes it possible in particular to maintain, where appropriate, a high concentration of HCl in the reactor and to thus increase the reaction rate.

The process according to the invention is preferably carried out in the liquid phase.

In a continuous process, the residence time, which is the ratio of the volume of liquid medium in the reactor to the flow rate by volume of the reactants, is generally greater than or equal to 1 hour. Advantageously, the residence time is greater than or equal to 5 hours. In a continuous process, the residence time, which is the ratio of the volume of liquid medium in the reactor to the flow rate by volume of the reactants, is generally less than or equal to 50 hours. Good results are also obtained with a residence time, as defined above, of 2 to 4 hours.

The residence time can alternatively be defined as the ratio of the volume of liquid medium in the reactor to the flow rate by volume of glycerol In this case, the residence time is generally greater than or equal to 1 hour, preferably greater than or equal to 5 hours. Advantageously, the residence time is greater than or equal to 10 hours. In this case, the residence time defined as the ratio of the volume of liquid medium in the reactor to the flow rate by volume of glycerol is generally less than or equal to 100 hours, preferably lower than or equal to 50 hours and most preferably lower than or equal to 30 hours. A residence time equal to or less than about 20 hours is particularly well suited.

In a batch process, the reaction time is generally from 1 to 20 hours.

In the process for producing a chlorinated organic compound according to the invention, at least dichloropropanol is preferably obtained as chlorinated organic compound.

The term "dichloropropanol" is generally intended to mean a mixture of isomers consisting essentially of 1,3-dichloropropane-2-ol and of 2,3-dichloropropane-1-ol.

In the process for producing a chlorinated organic compound according to the invention, a high selectivity for 1,3-dichloropropane-2-ol is surprisingly obtained, which isomer is particularly suitable as starting product for a dehydrochlorination with a view to producing epichlorohydrin. In this aspect of the process for producing a chlorinated organic compound according to the invention, the reaction medium generally comprises from 10 to 95% by weight of dichloropropanol. It preferably comprises from 50 to 90% by weight of dichloropropanol.

In one variant, which is particularly preferred in a continuous process, the liquid reaction medium comprises from 1 to 10% of dichloropropanol by weight relative to the total weight of the liquid reaction medium.

In another variant, which is particularly preferred in a continuous process, the liquid reaction medium comprises from 10 to 50% of dichloropropanol by weight relative to the total weight of the liquid reaction medium.

In the process for producing a chlorinated organic compound according to the invention, the reaction medium generally comprises from 1 to 50% by weight of water. It often comprises from 1 to 15% by weight of water. It preferably comprises at most 10% by weight of water. A water content of less than or equal to approximately 5% by weight is more particularly preferred.

In a particular aspect, the process for producing a chlorinated organic compound according to the invention is carried out continuously in a liquid reaction medium in which a water concentration of greater than or equal to 1% by weight relative to the total weight of the liquid reaction medium, preferably greater than or equal to 2% by weight, is maintained. In this particular aspect, the process for producing a chlorinated organic compound according to the invention is carried out continuously in a liquid reaction medium in which a water concentration of less than or equal to 15% by weight relative to the total weight of the liquid reaction medium, preferably of less than or equal to 10% by weight, is maintained. Maintaining a water concentration of less than or equal to 8% by weight is also possible.

In a first variant, the process for producing the chlorinated organic compound is carried out in the presence of at least one organic solvent such as a chlorinated organic solvent, a suitable alcohol, a ketone, an ester or an ether.

The amount of heavy compounds produced on synthesizing chlorodihydroxypropane and dichloropropanol staring from glycerol and from hydrogen chloride can be notably reduced using a non-aqueous solvent that is miscible with glycerol and the various reaction products. Particular examples of such non-reactive solvents are dichloropropanol, dioxane, phenol and cresol. Chlorodihydroxypropane is also suitable as a diluent of glycerol with the aim of producing dichloropropanol. A mixture of such solvents is also suitable and mixtures of chlorodihydroxypropane and of dichloropropanol are particularly preferred for the production of dichloropropanol starting from glycerol. The effect of the solvent is particularly advantageous if the glycerol content in the reaction medium is less than or equal to 50% by mass relative to the total mass of the reaction medium, and particularly good if this concentration is less than 30%. It is advantageously less than 10% by weight.

In this variant, the solvent content in the reaction medium is generally from 10 to 95% by weight, preferably from 30 to 80% by weight.

In a second variant, the process for producing the chlorinated organic compound is carried out in the presence of an organic solvent comprising or consisting of heavy byproducts of the reaction. By "heavy byproducts of the reaction", it is intended to denote, for example, glycerol oligomers which can be at least partially chlorinated and/or esterified. A mixture of heavy byproducts with at least an additional organic solvent such as cited above is particularly suitable.

In another variant of the process for producing a chlorinated organic compound according to the invention, vapour stripping, in particular steam stripping of the reaction medium, is carried out. In this case, it is possible to obtain a fraction containing from 1 to 5, some times from 2 to 3 and preferably from 1.5 to 2.5 mol/l of chlorinated organic compound, in particular of dichloropropanol. In this variant, the stripped mixture is mainly composed of water and dichloropropanol.

In a preferred variant, continuous or periodic withdrawal of a fraction comprising at least water and chlorinated organic compound, in particular dichloropropanol, is carried out.

Said fraction may also contain hydrogen chloride. Preferably, the fraction is withdrawn continuously as its constituents form. The fraction obtained can subsequently be subjected to an operation of separation by settling out.

In a particular variant, which is preferred when the reaction is carried out continuously and continuous or periodic withdrawal from the reaction of a fraction comprising at least water and chlorinated organic compound is carried out, the reaction medium is fed with water, in particular with steam. The feeding can be effected with extrinsic water originating from a suitable feed pipe or, optionally, with residual water recovered from another unit reaction or operation.

This feed is generally effected in such as way as to maintain the water concentration in the reaction medium within the ranges indicated above.

The variants involving continuous or periodic withdrawal can be effected by introducing into a distillation step a gaseous phase withdrawn starting from the reaction medium, in particular withdrawing and introducing into a distillation step a gas phase which is in equilibrium with a liquid reaction medium. Where appropriate, this embodiment can be carried out in a reactor surmounted by a suitable distillation column. This embodiment is particularly suitable when aqueous hydrochloric acid is used as chlorinating agent. It is also possible to arrange a distillation column separated from the reactor, the liquid bottom of which can be sent back to the reaction medium. This embodiment is particularly suitable when hydrogen chloride, for example gaseous or essentially anhydrous hydrogen chloride, is used as chlorinating agent.

In this embodiment, the operating conditions of the reactor such as feed rates of reactants, in particular hydrogen chloride and glycerol, catalyst feed rate, temperature, reactor volume and pressure are preferably adjusted in such a way that the concentration of hydrogen chloride in the mixture fed in distillation remains lower than the concentration of hydrogen chloride in the binary azeotropic hydrogen chloride-water mixture at the pressure of the reaction. An effective means of adjusting this concentration is controlling the hydrogen chloride supply to the liquid reaction medium.

This embodiment of the process is preferably carried out continuously.

In one aspect, the fraction to be introduced into the distillation column separated from the reactor is withdrawn continuously or periodically, preferably continuously, from the liquid reaction medium and at least water and chlorinated organic compound is separated. In the distillation step, a fraction containing chlorinated organic compound may also be separated. In addition, one or more fractions containing organic products such as heavy byproducts and in particular catalyst and/or hydrogen chloride can also be separated in this distillation step and generally recycled to the reaction medium. By selecting an appropriate reflux ratio, it is possible to separate in this aspect a fraction containing at least water which is substantially free of hydrogen chloride.

"Substantially free of hydrogen chloride", is understood to denote in particular a hydrogen chloride content in the fraction comprising water equal to or less than 10% by weight relative to the total weight of the fraction comprising water. Often, this content is equal to less than 5% by weight and preferably equal to or less than 1% by weight and more preferably equal to or less than 0.3% by weight. Generally, "substantially free of hydrogen chloride" is understood to denote in particular a hydrogen chloride content in the fraction comprising water equal to or more than 1 mg/kg, often equal to or more than 10 mg/kg relative to the total weight of the fraction comprising water. In this aspect, it is possible to eliminate water formed during the reaction and/or introduced with the reactants from the reaction medium while maintaining substantially all of hydrogen chloride and catalyst in the reaction medium.

The dichloropropanol, in particular the 1,3-dichloropropane-2-ol, forms pseudoazeotrope with water and hydrogen chloride. The invention also relates to this pseudoazeotropic composition.

Fundamentally, the thermodynamic state of a fluid is defined by four interdependent variables: the pressure (P), the temperature (T), the composition of the liquid phase (X) and the composition of the gaseous phase (Y). A true azeotrope is a particular system having 2 or more components, for which, at a given temperature and at a given pressure, the composition of the liquid phase X is exactly equal to the composition of the gaseous phase Y. A pseudoazeotrope is a system having 2 or more components, for which, at a given temperature and at a given pressure, X is substantially equal to Y. In practice, this means that the constituents of such pseudoazeotropic systems cannot be easily separated by distillation.

For the purposes of the present invention, is understood in particular by "pseudo-azeotropic composition", a composition which has the property that, when it is subjected to an evaporation operation, after 50% by weight of the composition has evaporated the vapour pressure of the remaining composition differs from the vapour pressure of the initial composition by less than or equal to 10%. Preferably, this difference is less than or equal to 5%.

Generally, the pseudoazeotropic composition according to the invention comprises from 43 to 63% by weight of water, from 23 to 43% by weight of 1,3-dichloropropane-2-ol and from 4 to 24% by weight of hydrogen chloride. A particular pseudo-azeotropic composition which is particularly difficult to separate by distillation may be characterized by its boiling temperature, which is 106° C. under 1011 mbar. It consists, at this temperature and pressure, of 53% by weight of water, of 33% by weight of 1,3-dichloropropane-2-ol and of 14% of hydrogen chloride. It was observed that this azeotropic composition separates, at temperatures of less than approximately 40° C., or even less than or equal to 25° C., into a dense organic phase and a lighter aqueous phase. The organic phase contains a considerable amount of 1,3-dichloropropane-2-ol, for example at least 50% by weight of the total weight of the organic phase, preferably at least 80% by weight, and the organic phase contains in addition water and hydrogen chloride. The aqueous phase contains water, hydrogen chloride and a minority amount of 1,3-dichloropropane-2-ol, for example at most 50% by weight of the total weight of the aqueous phase, preferably at most 30% by weight. An operation of decantation permits to separate the organic phase containing the dichloropropanol from the aqueous phase, this latter being recycled to the reflux of the distillation.

It has been found that the exploitation of the liquid-vapour equilibrium properties of the water-hydrogen chloride-dichloropropanol ternary composition makes it possible to withdraw from the production reaction the reaction products comprising in particular dichloropropanol and water, while at the same time allowing most of the catalyst(s) and of the reactants (including the hydrogen chloride), to be recycled to the reactor.

In a preferred embodiment, a separation of a fraction of the reaction medium is carried out by a distillation step and the sum of materials fed to this distillation step has a hydrogen chloride concentration which is lower than the hydrogen chloride concentration in the binary azeotropic composition hydrogen chloride/water at the pressure of the distillation.

In consequence, the invention concerns also a process for separation of a mixture containing at least water, dichloropropane and hydrogen chloride wherein the mixture is separated in a distillation step wherein the sum of materials fed to said distillation step has a hydrogen chloride concentration which is lower than the hydrogen chloride concentration in the binary azeotropic composition hydrogen chloride/water at the pressure of the distillation.

It is possible for example to control the hydrogen chloride content in the sum of materials fed to the distillation step by adding water. Such addition can be carried out for example by injection of vapour into the boiler of a distillation column used in the distillation step or by recycling to the distillation step of a water phase which can be obtained for example by decantation of a fraction withdrawn from the top of a distillation column.

The maximum suitable hydrogen chloride concentration decreases slightly when the operating pressure is higher in agreement with the liquid-vapour equilibrium data for the azeotropic hydrogen chloride published by Bonner and Titus (J. Amer. Chem. Soc. 52, 633 (1930)) and partially reprinted in the Table hereafter:

| Pressure (Torr) | Temperature (° C.) | HCl in azeotrope (% wt) |
|---|---|---|
| 50 | 48.74 | 23.42 |
| 250 | 85.21 | 21.88 |
| 370 | 90.24 | 21.37 |
| 540 | 99.65 | 20.92 |
| 760 | 108.58 | 20.22 |
| 1000 | 116.19 | 19.73 |
| 1220 | 122.98 | 19.36 |

In such conditions, a fraction comprising water which fraction is substantially free of hydrogen chloride as defined above can be recovered by distillation from the reaction mixture or the gas phase above the liquid reaction mixture, e.g. by distilling material withdrawn from said gas phase and obtaining the fraction comprising water preferably at the top of the distillation column.

For instance, at atmospheric pressure (101.3 kPa), it is possible to obtain by distillation of the reactor gas phase a binary azeotropic mixture of water and dichloropropanol containing 23% by weight of dichloropropanol if the hydrogen chloride concentration in that gas phase in contact with the reaction medium is lower than about 20.22% by weight.

When dichloropropanol is not completely removed from the reaction medium by withdrawal of a fraction containing water, it is possible to recover at least a fraction of the reaction medium containing dichloropropanol.

In this aspect of the process for producing a chlorinated organic compound according to the invention, at least one fraction comprising from 50 to 95% by weight of dichloropropanol and at most 50% by weight of water is generally recovered. Preferably, this fraction comprises from 75 to 99.9%, often from 75 to 99%, by weight of dichloropropanol and from 0.01 to 25%, often from 1 to 25%, by weight of water.

The recovery is preferably carried out by distillation or evaporation. Other fractions obtained during this step, comprising, for example, monochloro-propanediol and, optionally, glycerol and catalyst, can be recycled to the reaction with the chlorinating agent. It is also possible to separate at least one fraction containing heavy by-products of the reaction, such as described above, in particular chlorinated polyglycerols, which can be destroyed or can optionally be used in a process for producing polyglycerols, for example by dechlorination.

The distillation or evaporation is generally carried out at a temperature of at least 20° C. This temperature is often at least 60° C. It is preferably at least 70° C. The distillation or evaporation is generally carried out a temperature of at most 180° C. This temperature is preferably at most 140° C.

The distillation or evaporation is generally carried out at a pressure of greater than 0.001 bar. This pressure is preferably greater than or equal to approximately 0.003 bar. The distillation or evaporation is generally carried out at a pressure of at most 1 bar. This pressure is often at most 0.5 bar. It is preferably at most 0.2 bar.

The distillation or evaporation operation can be carried out either by means of distillation columns or by means of evaporators, of film evaporators or alternatively of wiped thin film evaporators. The recoverable fractions of the residues can be separated therefrom advantageously by means of a wiped thin film evaporator with an interior or exterior condenser.

In a particular variant, the dichloropropanol is produced according to a process comprising:

(a) a first reaction step in which glycerol is brought into contact with the chlorinating agent so as to obtain a fraction of products comprising at least chloropropanediol;

(b) optionally at least part of the fraction of products is subjected to a drying operation;

(c) at least part of the fraction of optionally dried products is introduced into a second reaction step in which at least part of the chloropropanediol is reacted with the chlorinating agent.

Steps (a) and (c) in this variant are preferably carried out under conditions and with the preferences as described above for the process for producing a chlorinated organic compound according to the invention. However, it is preferred to carry out the reaction of step (a) in the presence of water at a concentration preferably ranging from 20 to 80% by weight relative to the total weight of the reaction medium.

Step (b) can be carried out, for example, by a stripping operation in at least one of the reactors of steps (a) or (c) or by means of an evaporator placed on a recirculation pipe exterior to the reactor. According to another preferred variant, the water is removed by means of a membrane technique.

The process for producing an organic compound, in particular dichloropropanol, according to the invention can be carried out, for example, in cascade reactors, in at least one plate column or in at least one bubble column, or an assembly of such reactors.

The reactors may effectively be of a type that is stirred either by means of internal stirring, or by means of a recirculation pipe exterior to the reactor.

When, in the process according to the invention, the reaction medium is heated, the heating can be obtained, for example, by means of a jacket or by means of an internal heat exchanger. Heating can also be obtained by means of a heat exchanger on a recirculation pipe exterior to the reactor. Optionally, the heating is obtained by combined use of a jacket and of a heat exchanger on a recirculation pipe exterior to the reactor.

In particular when the process according to the invention is operated in a continuous or fed-batch mode, secondary reactions can lead to the build-up in the reactor of by-products of low volatility, among which more or less chlorinated glycerol oligomers. This build-up can lead to a progressive increase of the volume of the reaction medium and require a continuous or discontinuous purge of the reactor to keep the volume at an adequate level.

If appropriate, the catalyst quantity which is removed during such purging operation can be compensated by the introduction of an equivalent quantity of pure or purified catalyst.

The catalyst contained in the purge from the reaction mixture can be economically recycled in the reactor after a purification treatment. For example, catalysts with low solubility in water can be subjected to an acid hydrolysis treatment, preferably carried out at a temperature higher than 30° C., preferably at least 50° C. which is followed by a separation step e.g. by decantation, filtration or extraction. It has been found that in the case of adipic acid, an acid hydrolysis of the purge leads after cooling and filtration, to the recovery of crystallised adipic acid of high purity with a good yield.

When anhydrous HCl is used, it is preferred to direct a liquid stream comprising the glycerol against the current of the stream of HCl. When the process is carried out in several reactors, the HCl is advantageously dried between two reactors, for example by adsorption on a suitable solid, such as a molecular sieve, or by reverse osmosis through a suitable membrane.

This particular embodiment of the process according to the invention makes it possible to obtain, particularly economically, concentrated dichloropropanol often having a dichloropropanol content of greater than or equal to 90% by weight relative to the total weight of the dichloropropanol. By means of this approach, it is possible to obtain 1,3-dichloropropane-2-ol as major isomer with an isomeric purity of greater than 80%.

In a particular embodiment of the present invention, when dichloropropanol is obtained in the process for producing a chlorinated organic compound according to the invention, part of this dichloropropanol can be subjected to a dehydrochlorination operation in the presence of at least one other alcohol, more particularly in the presence of polyols, such as, for example, bisphenol A, so as to obtain "epoxy" resins or useable monomers thereof. The major isomer of the process for producing dichloropropanol according to the invention, 1,3 dichloropropanol, is particularly suitable for this operation since it makes it possible to conserve a linear structure of the polymer or monomer thus obtained This is not the case of the 2,3-isomer obtained as majority product by the current industrial processes.

The invention also relates to the use of a dichloropropanol containing at least 50% by weight of 1,3-dichloropropane-2-ol relative to the total dichloropropanol, as starting product for producing organic compounds such as, in particular, epichlorohydrin or epoxy resins. In this use, the 1,3-dichloropropane-2-ol content is often greater than or equal to 75% by weight relative to the total dichloropropanol. Preferably, this content is greater than or equal to 80% by weight. Good results have been obtained with a dichloropropanol containing at most approximately 99% by weight, or even at most approximately 95% by weight, of 1,3-dichloropropane-2-ol relative to the total dichloropropanol. It is also possible to use dichloropropanol consisting essentially of 1,3-dichloropropane-2-ol.

In a particular embodiment, when dichloropropanol is obtained in the process for producing a chlorinated organic compound according to the invention, at least part of this dichloropropanol is preferably subsequently subjected to a dehydrochlorination operation so as to obtain epichlorohydrin.

The processes for producing epichlorohydrin that are generally used, for example starting with allyl chloride, produce epichlorohydrin containing chlorinated organic impurities such as, for example, trichloropropane, trichloropropene, dichloropropene or 2-chloroprop-2-en-1-ol, which impurities have drawbacks when the epichlorohydrin is used in certain qualities of epoxy resins. This type of impurities is present, where appropriate, in a greatly reduced concentration in the epichlorohydrin obtained according to the invention. The process according to the invention therefore makes it possible to produce highly pure epichlorohydrin containing fewer bothersome impurities.

In particular, the epichlorohydrin may exhibit a purity of greater than or equal to 99.5% by weight.

It has been noted that the 1,3-dichloropropane-2-ol which can be obtained as majority product according to the invention possesses a reactivity in a dehydrochlorination reaction, in particular a basic dehydrochlorination, that is greater than its 2,3-dichloropropane-1-ol isomer obtained as majority product by the current industrial processes. This aspect makes it possible to improve the selectivity of the dehydrochlorination operation by reducing the residence time of the reactants in the synthesis medium.

Moreover, the process according to the invention makes it possible to reduce the volume of the aqueous effluents of an epichlorohydrin production and also to minimize the content of these effluents in organochlorinated by-products such as, for example, chlorinated ethers.

1,3-Dichloropropan-2-ol is surprisingly relatively unreactive with epichlorohydrin and does not give rise to the formation of a significant amount of organochlorinated by-products during the synthesis of epichlorohydrin.

The use of purified 1,3-dichloropropane-2-ol, in particular having the 1,3-dichloropropane-2-ol contents specified above, in epichlorohydrin synthesis makes it possible to further improve the quality of the production effluents by dramatically reducing the formation of chlorinated impurities.

According to a particular embodiment, the epichlorohydrin is produced in an aqueous reaction medium, fed with from 1 to 30% by weight of dichloropropanol relative to the total feed.

According to another embodiment, that is preferred, the reaction medium of the process for producing epichlorohydrin according to the invention is fed with from 30 to 90 weight % of dichloropropanol relative to the total feed. In the latter variant, the reaction medium is often fed with from 60 to 90 weight % of dichloropropanol, preferably from 65 to 80 weight %. It is also possible to advantageously carry out a feed with from 30 to 65% by weight of dichloropropanol relative to the total feed.

This embodiment makes it possible in particular to considerably reduce the water waste of the process.

In another particular variant of the process for producing epichlorohydrin according to the invention, the dichloropropanol is used in stoichiometric or substoichiometric quantities relative to the base. In this case, at least 1 equivalents of base per equivalent of dichloropropanol is generally used. At least 1.5 equivalents of base per equivalent of dichloropropanol are often used. In this case, at most 5 equivalents of base per equivalent of dichloropropanol are generally used.

In still another particular variant of the process for producing epichlorohydrin according to the invention, the dichloropropanol is used in excess relative to the base, which makes it possible to improve the yield. In this case, at least 1.1 equivalents of dichloropropanol per equivalent of base are generally used. At least 1.5 equivalents of dichloropropanol per equivalent of base are often used. At least 2 equivalents of dichloropropanol per equivalent of base are preferably used. In this case, at most 5 equivalents of dichloropropanol per equivalent of base are generally used.

Other reactants that are fed into the process for producing epichlorohydrin according to the invention are preferably chosen from aqueous solutions, in particular concentrated solutions of at least one base preferably chosen from NaOH, $Ca(OH)_2$ and purified caustic brine. The expression "purified caustic brine" is intended to denote caustic soda which can contain NaCl such as produced by a diaphragm based electrolysis process. The content of base in the solution or the slurry is, in this case, generally at least 5% by weight, preferably at least 10% by weight and most preferably equal to or more than about 20% by weight. This content is generally less than or equal to 60% by weight. A content of approximately 50% by weight is very suitable.

The feed may also contain an organic solvent such as a ketone or an ether, for example methyl ethyl ketone.

A single feed or, preferably, a feed in stages, for example with two or three feed points, can be carried out.

The medium in this reaction embodiment may be a single-phase medium or, in particular when an organic solvent is used, a two-phase medium.

In a particular variant, an at least partial feed of water recovered optionally from the process for producing dichloropropanol described above is carried out. This water can, for example, be used to generate basic solution or slurry.

In the process for producing epichlorohydrin according to the invention, the reaction is generally carried out at a temperature of at least 0° C. This temperature is often at least 20° C. It is preferably at least 30° C. In the process for producing epichlorohydrin according to the invention, the reaction is generally carried out at a temperature of at most 140° C. It is preferably at most 120° C. In a first particular variant, the temperature is from 25 to 50° C. In a second particular variant, the temperature is from 60 to 100° C.

In the process for producing epichlorohydrin according to the invention, it is particularly advantageous to at least partially recover water possibly present at the end of the dehydrochlorination, for example by evaporation or by reverse osmosis. This recovery, described below, can also be used in other dehydrochlorination processes, in particular in processes using a basic solution or slurry.

By means of this recovery operation, it is possible to obtain an aqueous fraction enriched in salts, in particular in NaCl, and a fraction rich in water. The fraction enriched in salts can be recovered and used, optionally after a suitable purification step, for example in an electrolysis plant for producing chlorine, or it can be introduced into an optionally oxidative treatment intended to reduce its content of organic compounds possibly present, and eliminated from the plant. It is also possible to carry out an evaporation to dryness and, preferably, to eliminate the salt recovered in solid form. The fraction rich in water can be used advantageously for producing, where appropriate, the basic aqueous solution or slurry for use in the process for producing epichlorohydrin according to the invention.

In a particular aspect, salt, in particular NaCl is eliminated or recovered, during the dehydrochlorination operation, in an amount not exceeding 5, often not exceeding 2, preferably not exceeding 1.2, but generally of at least 1 mol of NaCl per mole of epichlorohydrin produced. The NaCl is often eliminated substantially exclusively during the dehydrochlorination step.

The invention also relates to a process for producing polyglycerol, according to which glycerol obtained from renewable raw material is used, in accordance with the use according to the invention, as starting product and said glycerol is preferably brought into contact with at least one condensing agent or with epichlorohydrin in the presence of a base. Suitable conditions for the latter reaction are described in U.S. Pat. Nos. 4,960,953 and 5,041,688 in the Applicant's name.

The condensing agent may be an acidic or basic agent. A solid condensation catalyst may optionally be used.

In the process for producing polyglycerol according to the invention, epichlorohydrin derived from the process for producing epichlorohydrin according to the invention described above is preferably used.

The invention also relates to a process for producing epoxy resins, according to which epichlorohydrin derived from the process for producing epichlorohydrin according to the invention described above is reacted with an alcohol and/or a polyol. The production of epoxy resins is described, for example, in Ullmann's Encyclopedia of Industrial Chemistry, 5. ed., Vol. A9, p. 547-562.

The invention also relates to a process for producing biodiesel and an organic compound, according to which:

(a) a plant oil is subjected to a trans-esterification reaction with an alcohol other than glycerol, preferably methanol or ethanol, so as to recover at least biodiesel and a crude product comprising glycerol;

(b) the crude product is optionally subjected to a purification operation such as distillation;

(c) glycerol formed in step (a) is subjected to the process for producing an organic compound according to the invention.

In another process step (a) can consist of subjecting a plant oil to a hydrolysis reaction with water, for example under superatmospheric pressure, so as to produce at least a mixture of fatty acids and a crude product comprising glycerol and obtaining biodiesel by esterification of the fatty acid mixture.

In a first variant of the process for producing biodiesel and an organic compound according to the invention, at least steps (a) and (c) are carried out on the same production site.

In a second variant of the process for producing biodiesel and an organic compound according to the invention, steps (a) and (c) are carried out on different production sites. Step (c) is advantageously located in the vicinity of a source of chlorine or of hydrogen chloride.

Figure 1:
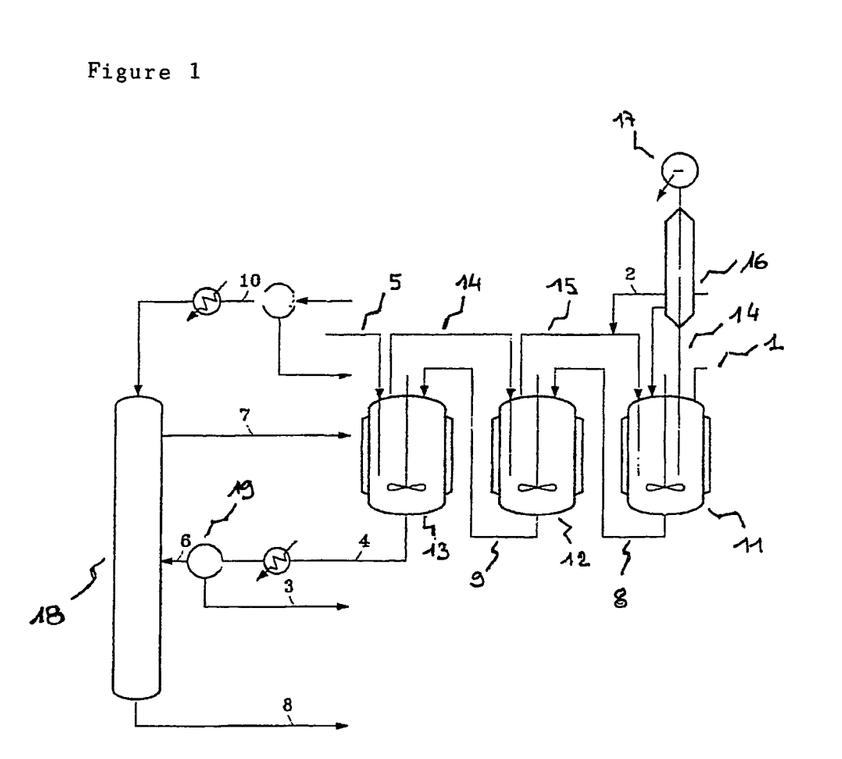
FIG. 1 shows a particular scheme for a plant that can be used for carrying out the process for producing a chlorinated organic compound according to the invention.

FIG. 1 shows a particular scheme for a plant that can be used for carrying out the process for producing a chlorinated organic compound according to the invention. This plant comprises 3 reactors. The first reactor (11) is fed through line (1) with glycerol and with a catalyst. The liquid bottom of this first reactor feeds the second reactor (12) via line (8), and the second feeds the third (13) via line (9). The gaseous HCl is fed through line (5) into the third reactor, the degassing of the latter feeds, in liquid phase, the second reactor via line (14), the degassing of which itself feeds the first reactor via line (15). In each reactor, the water formed by the reaction is eliminated as it is produced, with the degassing of the reactors. All the water therefore leaves by means of the degassing of the first reactor.

Particularly preferred temperatures and residence time are 100° C. and 3 hours for reactor (11) and 130° C. and 8 hours for reactor (12) and 130° C. and 8 hours for reactor (13) as indicated in FIG. 1.

The degassing of the first reactor involves a column (16), the residue of which is sent back to this reactor. The water whose acid has been removed exits at the head of the column (17). The dichloropropanol accompanying the water by azeotropy is separated therefrom by settling out and is recycled to the second reactor via line (2).

The dichloropropanol, the catalyst and the heavy products leaving the third reactor are then separated by distillation in the column (18), the dichloropropanol can be withdrawn at the top via line (7), the catalyst and the heavy products can be withdrawn at the bottom via line (8). The column preferably functions under a vacuum of 0.1 bar.

The column feed can be filtered via filter (19) so as to remove solid particles possibly present in crude glycerol.

The heavy products of column (18) may or may not be recycled to the reactor (11).

Figure 2:
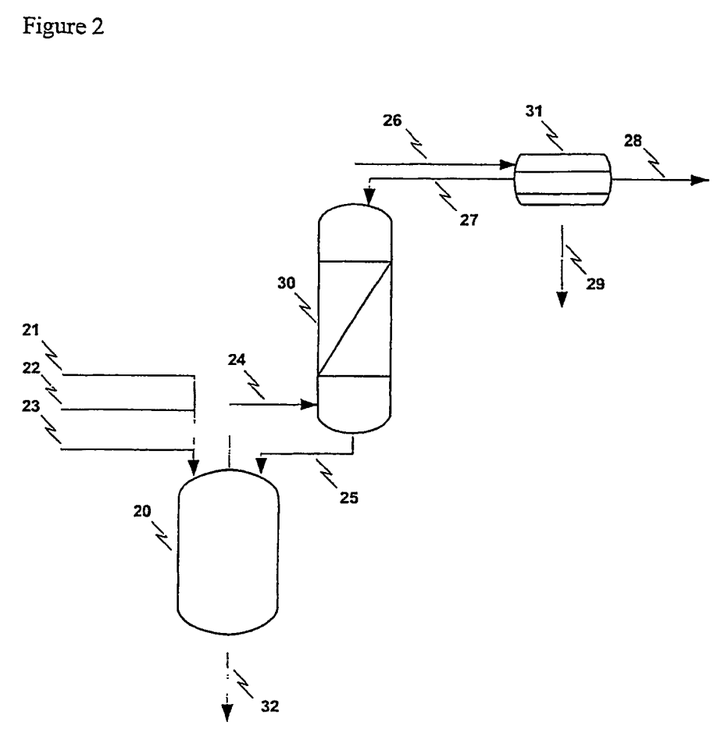
FIG. 2 shows a preferred particular scheme for a plant that can be used for carrying out the process for producing dichloropropanol according to the invention.

FIG. 2 shows a preferred particular scheme for a plant that can be used for carrying out the process for producing dichloropropanol according to the invention: A reactor (20) is fed, in a continuous or batch mode, with glycerol via line (21) and catalyst via line (22), the feed of hydrogen chloride, anhydrous or in aqueous solution, is carried out continuously or in batch-mode via line (23), A distillation column (30) is fed via line (24) with vapour produced from reactor (20), A stream is withdrawn from column (30) via line (26) and fed to decantor (31) in which aqueous and organic phases are separated. A fraction of the separated aqueous phase is optionally recycled via line (27) to the top of the column for maintaining reflux The production of dichloropropanol is distributed between the organic phase withdrawn through line (29) and the aqueous phase withdrawn through line (28). The residue from column (30) can be recycled to the reactor via line (25). Heavy by-products can optionally be removed from the reactor by means of a purge (32) located in the liquid bottom of the reactor.

Results obtained according to this scheme are detailed in example 12.

This variant of the process allows to remove at the top by azeotropy almost all of the water arising from the reaction, from the starting materials and/or possibly fed in the bottom of the reactor or of the column and to obtain a mixture of dichloropropanols of very high purity, above 99.5% by weight for the sum of the two isomers, with a selectivity related to hydrocarbon chain and hydrogen chloride higher than 99% by weight.

Figure 3:
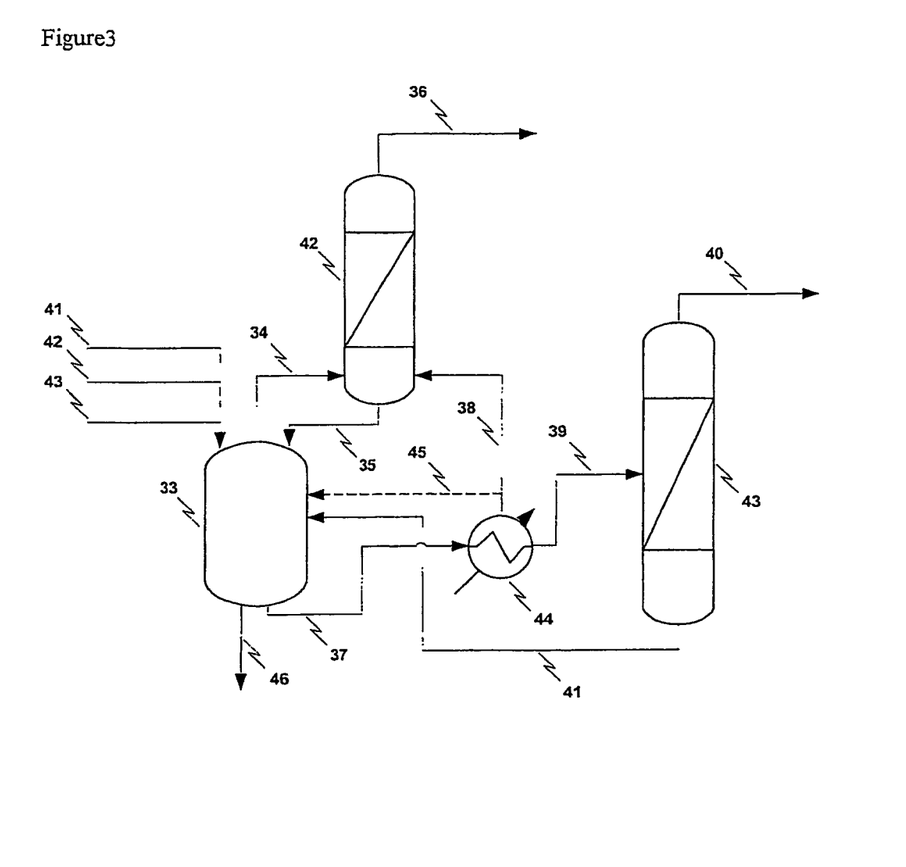
FIG. 3 shows a more preferred scheme for a plant that can be used for carrying out the process for producing dichloropropanol according to the invention.

FIG. 3 shows a more preferred scheme for a plant that can be used for carrying out the process for producing dichloropropanol according to the invention a reactor (33) is continuously or batch fed with glycerol via line (41) and catalyst via line (42), the feed of hydrogen chloride, anhydrous or in aqueous solution, is carried out continuously or in batch-mode through line (43), a distillation column (42) is fed via line (34) with the vapour produced from reactor (33), the residue from column (42) is recycled via line (35) to the reactor (33), a purge from the reactor bottom is fed via line (37) into a stripper (44) wherein a partial stripping operation is carried out e.g. by heating or by gas sweeping with nitrogen or steam, the gas phase containing most of the hydrogen chloride from stream (37) is recycled via line (38) to the column (42) or via line (45) to the reactor (33), a distillation or stripping column (43) is fed with the liquid phase arising from the stripper (44) via line (39), the main fraction of dichloropropanols is collected from the top of the column through line (40) and the column residue is recycled via line (41) to the reactor (33). Stripping can be carried out with nitrogen or steam or by heat. Heavy by-products can optionally be removed from the reactor by means of a purge (46) located in the liquid bottom of the reactor.

This variant of the process allows to remove at the top by azeotropy almost all of the water arising from the reaction, from the starting materials and/or possibly fed in the bottom of the reactor or of the column. In addition to the advantages presented by the previous scheme, this more preferred scheme related to the previous one, allows a limited steam consumption.

The examples below are intended to illustrate the invention without, however, limiting it.

EXAMPLE 1

A mixture of 453 g of glycerol (4.92 mol) and of 29.5 g of glacial acetic acid (0.49 mol) was heated at 110° C. with stirring for 20 minutes. Anhydrous hydrogen chloride was then blown into this mixture according to a programmed flow rate of 5.2 mol/h for 2 h, 3.8 mol/h for 100 min and, finally, 1.3 mol/h for 317 min. In total, 23.6 mol of hydrogen chloride were introduced. The analysis of the reaction mixture at the end of trial appears in Table 1. The rate of conversion of the glycerol was 99.1% and the selectivity in terms of heavy products related to the glycerol (diglycerol and chlorinated diglycerol) related to the glycerol comes to 0.4%.

EXAMPLE 2

A mixture of 110 g of glycerol (1.20 mol), of 257 g of 1-chloro-2,3-dihydroxypropane (2.32 mol) and of 21 g of glacial acetic acid (0.35 mol) was heated at 110° C. with stirring for 20 minutes. Anhydrous hydrogen chloride was then blown into this mixture according to a flow rate successively set at 4.76 mol/h for 26 min, 2.04 mol/h for 71 min, 0.62 mol/h for 4 h and, finally, 0.3 mol/h for 10 h. In total, 10.0 mol of hydrogen chloride were introduced. The analysis of the reaction mixture at the end of trial appears in Table 1. The rate of conversion of the glycerol was 99.5% and the selectivity in terms of heavy products (diglycerol and chlorinated diglycerol) was 0.03%.

TABLE 1

|  | Trial 1 (g/kg) | Trial 2 (g/kg) |
|---|---|---|
| Glycerol | 4.6 | 0 |
| 1-Chloro-2,3-dihydroxypropane | 166 | 55 |
| 2-Chloro-1,3-dihydroxypropane | 40 | 6.6 |
| 1,3-Dichloropropan-2-ol | 475 | 711 |
| 2,3-Dichloropropan-1-ol | 11 | 20.8 |
| Diglycerol | 1 | 0 |
| Monochlorinated diglycerol | 3 | 0.4 |
| Acetic acid | 21 | 23 |
| Organic acetates | 43 | 29.5 |
| Water | 178 | 121 |
| Hydrochloric acid | 58.8 | 57.7 |

EXAMPLES 3-7

Aqueous hydrochloric acid, glycerol, an organic acid and dichloropropanol were introduced at a constant flow rate into a 350 ml glass reactor thermostatted at the trial temperature. The reactor, which functioned at atmospheric pressure, was equipped with an overflow system for maintaining a constant volume of liquid. The reaction mixture fraction that was vaporized was evacuated from the reactor and condensed at ambient temperature. The condensate separated into 2 phases: a dense organic phase containing mainly dichloropropanol and a lighter aqueous phase containing most of the hydrochloric acid which had not reacted. The liquid mixture collected at the overflow outlet contained the remainder of the dichloropropanol production.

Example 3 describes the use of concentrated hydrochloric acid with acetic acid as catalyst Most of the catalyst used (55%) evaporated from the reaction liquid and was found in the condensate.

Example 4 illustrates the improvement provided by replacing the acetic acid with caprylic acid. A more limited fraction (10%) of the acid was in this case found to be evaporated from the reactor.

Examples 5 to 7 demonstrate the effect of the reaction temperature. The best results were obtained above 120° C.

EXAMPLES 8 TO 11

The reactor described for Examples 3 to 7 was modified so as to be surmounted by a distillation column for rectifying the reaction medium fraction vaporized. Only the hydrochloric acid, the glycerol and the catalyst were introduced into the reactor at a constant flow rate. The reflux rate of the column was fixed at 50%. The results obtained using azeotropic hydrochloric acid diluted with an amount of water sufficient to produce the azeotropic entrainment of the dichloropropanol formed are given in detail in the table, under Examples 8 to 10. Optimal hydrochloric acid conversion and dichloropropanol selectivity was observed at around 130° C. Analysis of the distilled fractions indicates hardly more than a contamination of the dichloropropanol with a limited amount of carboxylic acid Example 11 illustrates the excellent results obtained with adipic acid.

The various control parameters and also the results obtained in trials 3 to 11 are given in detail in Table 2.

higher than 0.1%. The hydrochloric acid content of the aqueous phase was 0.037% and the adipic acid content was 18 mg/kg.

EXAMPLE 13

Purification of Adipic Acid from the Reaction Mixture Purge

A reaction mixture sampled from the continuous process and which composition is reprinted in the here below table has been subjected to a hydrolysis treatment.

|  | Unit | Concentration |
|---|---|---|
| HCl | (g/kg) | 1.4 |
| water | (g/kg) | 50.0 |
| dichloropropanol | (g/kg) | 271 |

|  |  | Continuous trial No. | | | | | | | | |
|---|---|---|---|---|---|---|---|---|---|---|
|  |  | 3 | 4 | 5 | 6 | 7 | 8 | 9 | 10 | 11 |
| Boiler temperature | ° C. | 123 | 121 | 123.1 | 130 | 117.6 | 146.4 | 130 | 119.4 | 131.6 |
| Concentrated aq. HCl | mol/kg | 9.59 | 9.59 | 5.29 | 5.29 | 5.29 | 3.95 | 3.95 | 3.95 | 3.94 |
| Nature of the organic acid |  | acetic | caprylic | caprylic | caprylic | caprylic | caprylic | caprylic | caprylic | adipic |
| Feed flow rates |  |  |  |  |  |  |  |  |  |  |
| Glycerol | g/h | 30 | 30 | 30 | 30 | 30 | 22 | 22 | 22 | 25.6 |
| 1,3-dichloropropane-2-ol | g/h | 42 | 42 | 42 | 42 | 42 | 0 | 0 | 0 | 0 |
| Organic acid | g/h | 3.9 | 9.41 | 9.41 | 9.41 | 9.41 | 6.21 | 6.21 | 6.21 | 3.6 |
| Aq. HCl | g/h | 79 | 79.5 | 149 | 163 | 148 | 98.7 | 98.7 | 98.7 | 153.5 |
| Overall conversions and selectivities |  |  |  |  |  |  |  |  |  |  |
| HCl conversion rate | (%) | 57.3 | 60.7 | 51.2 | 45.9 | 36.3 | 80.0 | 91.6 | 87.4 | 87.6 |
| Glycerol conversion rate | (%) | 87.8 | 91.8 | 93.0 | 95.2 | 86.4 | 97.7 | 96.7 | 95.0 | 99.4 |
| Org. Ac. in distillate/Org. Ac. used | mol/mol | 0.55 | 0.02 | 0.11 | 0.13 | 0.16 | 0.11 | 0.14 | 0.20 | <0.0005 |
| Monochloropropanediol selectivity | (%) | 61.9 | 56.0 | 51.0 | 57.2 | 47.0 | 27.8 | 29.6 | 25.1 | 7.4 |
| Dichloropropanol selectivity | (%) | 29.7 | 27.1 | 29.5 | 39.7 | 20.4 | 42.8 | 60.3 | 55.2 | 82.3 |
| Oligomer selectivity | (%) |  | 0.9 | 0.4 | 0.6 | 0.8 | 0.6 | 1.2 | 1.6 | 1.1 |

EXAMPLE 12

FIG. 2

Reactor (20) has been continuously fed with glycerol and a 33% by weight hydrochloric acid solution with relative flow rates mass ratios of 1/2.36. The residence time was 20 hours, the adipic acid concentration in the reaction medium was 3 mol of acid functionalities/kg. The reactor has been operated at atmospheric pressure and at 130° C. A vapour phase containing 55.3% of water, 9.1%/hydrogen chloride, 9.4% of dichloropropanol and 25.1% glycerol monochlorohydrin has been generated. The liquid phase of the reaction mixture contained 7.7% of water and 1.24% of hydrogen chloride. The gas phase removed from column (3) has been condensed at 25° C. and decanted in decanter (31). Reflux ratio was adjusted to withdraw the entire production of dichloropropanol at the top of column by recycling an appropriate amount of the aqueous phase from the decanter.

At the outlet of the decanter an aqueous phase containing 15.0% of dichloropropanol and an organic phase containing 88% of dichloropropanol were recovered. The yield of dichloropropanol was 93%. The analyses of both phases did not reveal any organic contaminant which content would be -continued

|  | Unit | Concentration |
|---|---|---|
| 3-chloro-1,2-propanediol | (g/kg) | 71 |
| 2-chloro-1,3-propanediol | (g/kg) | 13 |
| glycerol | (g/kg) | 3 |
| adipic acid | (g/kg) | 26 |
| diglycerol dichlorohydrine | (g/kg) | 0.9 |
| diglycerol | (g/kg) | <1 |
| dichloropropanol adipate monoester | (g/kg) | 96 |
| glycerol monochlorohydrine adipate monoester | (g/kg) | 108 |
| glycerol adipate monoester | (g/kg) | 6.7 |
| diglycerol dichlorohydrine adipate monoester | (g/kg) | 64 |
| diglycerol monochlorohydrine adipate monoester | (g/kg) | 8.8 |
| carboxylic acid + carboxylic esters (groups) | (mol/kg) | 4.54 |

250 g of this sample have been placed in a round bottom flask fitted with a Dean-Stark separator. Azeotropic hydrogen chloride (100.2 g) and water (36.26 g) have been added to the flask. The mixture was refluxed for 10 h. After that treatment, 79.2 g of organic phase containing 88% of dichloropropanol and 12% of water have been obtained in the Dean-Stark as well as 18.1 g of an aqueous phase saturated with 15% of dichloropropanol. The flask contained 284 g of a mixture which has been fractioned at 100° C.

A first fraction of the hydrolyzed mixture (134.3 g) has been cooled to room temperature under stirring. After 1.5 hour, 41.9 g of a crystalline white solid have been isolated by filtration. After 20 more hours, a new crop of 6.7 g of crystals is isolated from the first filtrate. Compositions of both solids and of the second filtrate are detailed in the next Table. Adipic crystals of 80 to 84% purity have been obtained with a recovery yield of 87%.

|  | Unit | Solid 1 | Solid 2 | 2nd filtrate |
|---|---|---|---|---|
| HCl | (g/kg) | 18.3 | 19.2 | 75.6 |
| water | (g/kg) | 63.5 | 80.5 | 338 |
| dichloropropanol | (g/kg) | 42 | 50 | 184 |
| 3-chloro-1,2-propanediol | (g/kg) | 41 | 51 | 176 |
| 2-chloro-1,3-propanediol | (g/kg) | 13 | 16 | 55 |
| glycerol | (g/kg) | 8.3 | 12 | 36 |
| adipic acid | (g/kg) | 843 | 801 | 33 |
| diglycerol dichlorohydrine | (g/kg) |  |  | 2.4 |
| diglycerol | (g/kg) | 1.2 | 0.8 | 1.8 |
| dichloropropanol adipate monoester | (g/kg) | 0.8 | 1 | 4.2 |
| glycerol monochlorohydrine adipate monoester | (g/kg) | 9.7 | 14 | 38 |
| glycerol adipate monoester | (g/kg) | 2.7 | 3.7 | 14 |
| diglycerol dichlorohydrine adipate monoester | (g/kg) | 1.5 | 2.3 | 6 |
| diglycerol monochlorohydrine adipate monoester | (g/kg) | 1.1 | 1.6 | 4.3 |
| carboxylic acid + carboxylic esters (groups) | (mol/kg) | 11.27 | 10.59 | 1.12 |

A second fraction of the hydrolyzed mixture (114.7 g) has been cooled to room temperature under stirring after being added with 28.2 g of water. After 1.5 hour, 27.7 g of a crystalline white solid have been isolated by filtration. After 20 more hours, a new crop of 7 g of crystals has been isolated from the first filtrate. A dilution by water leads to purer adipic acid crystals (purity of 91-93%) but with a lower global recovery yield of 75%. The recovered solid did not contain heavy by-products

|  | Unit | Solid 1 | Solid 2 | 2nd filtrate |
|---|---|---|---|---|
| HCl | (g/kg) | 8.5 | 8.7 | 55.4 |
| water | (g/kg) | 54.5 | 28.5 | 499.0 |
| dichloropropanol | (g/kg) | 24 | 21 | 136 |
| 3-chloro-1,2-propanediol | (g/kg) | 22 | 24 | 135 |
| 2-chloro-1,3-propanediol | (g/kg) | 7 | 7.5 | 43 |
| glycerol | (g/kg) | 5.1 | 5.6 | 28 |
| adipic acid | (g/kg) | 912 | 928 | 62 |
| diglycerol dichlorohydrine | (g/kg) | 0 | 0 | 2.1 |
| diglycerol | (g/kg) | <0.5 | 0 | 0.5 |
| dichloropropanol adipate monoester | (g/kg) | 0 | 0 | 1.7 |
| glycerol monochlorohydrine adipate monoester | (g/kg) | 0 | 0 | 18 |
| glycerol adipate monoester | (g/kg) | 0 | 0 | 6.9 |
| diglycerol dichlorohydrine adipate monoester | (g/kg) | <0.5 | 0 | 0.5 |
| diglycerol monochlorohydrine adipate monoester | (g/kg) | 0 | 0 | 0.5 |
| carboxylic acid + carboxylic esters (groups) | (mol/kg) | 12.38 | 13.46 | 1.16 |

The invention claimed is:

1. A process, comprising subjecting glycerol to a reaction with a chlorinating agent in the presence of a carboxylic acid catalyst to produce dichloropropanol, wherein the carboxylic acid catalyst is selected from the group consisting of glutaric acid and adipic acid.

2. The process according to claim 1 wherein the carboxylic acid catalyst is glutaric acid.

3. The process according to claim 1 wherein the carboxylic acid catalyst is adipic acid.

4. The process according to claim 1 wherein glycerol is subjected to a reaction with a chlorinating agent, with the addition of the carboxylic acid catalyst.

5. The process according to claim 1 wherein the process is carried out in a reactor and wherein the carboxylic acid catalyst is introduced in the reactor.

6. The process according to claim 1, wherein the chlorinating agent is an aqueous solution of hydrogen chloride with a hydrogen chloride content higher than or equal to 4% by weight.

7. The process according to claim 1, wherein the chlorinating agent comprises substantially anhydrous hydrogen chloride.

8. The process according to claim 5 wherein the carboxylic acid catalyst is a pure or purified carboxylic acid catalyst and the carboxylic acid catalyst is introduced into the reactor in solution in one of the reactants.

9. The process according to claim 8 wherein the reactant is glycerol.

10. The process according to claim 8 wherein the reactant is aqueous hydrochloric acid.

11. The process according to claim 5 wherein the carboxylic acid catalyst is a pure or purified carboxylic acid catalyst and the carboxylic acid catalyst is introduced into the reactor in a solvent selected from water, glycerol monochlorohydrin and dichloropropanol.

12. The process according to claim 1, wherein the reaction is carried out continuously.

13. The process according to claim 1, wherein the reaction is carried out in the liquid phase.

14. The process according to claim 1, further comprising subjecting the dichloropropanol to a dehydrochlorination reaction to produce epichlorohydrin.

15. The process according to claim 14, further comprising reacting the epichlorohydrin to produce an epoxy resin.

16. The process according to claim 1 wherein the chlorinating agent comprises hydrogen chloride.

* * * * *

UNITED STATES PATENT AND TRADEMARK OFFICE
CERTIFICATE OF CORRECTION

| | |
|---|---|
| PATENT NO. | : 8,415,509 B2 |
| APPLICATION NO. | : 10/580003 |
| DATED | : April 9, 2013 |
| INVENTOR(S) | : Krafft et al. |

It is certified that error appears in the above-identified patent and that said Letters Patent is hereby corrected as shown below:

Title page, Item 75 should read:

-- Philippe Krafft, Rhode Saint Genèse (BE);
Patrick Gilbeau, Braine-le-Comte (BE);
Benoît Gosselin, Tavaux (FR) --

Signed and Sealed this
Twelfth Day of November, 2013

Teresa Stanek Rea
*Deputy Director of the United States Patent and Trademark Office*